US011499934B2

(12) United States Patent
Yee et al.

(10) Patent No.: US 11,499,934 B2
(45) Date of Patent: Nov. 15, 2022

(54) MOLD DETECTING DEVICE USING SENSOR TO MEASURE ELECTRICAL PROPERTIES

(71) Applicant: Robert Bosch GmbH, Stuttgart (DE)

(72) Inventors: Seow Yuen Yee, Mountain View, CA (US); Franz Laermer, Weil der Stadt (DE); Christian Peters, Mountain View, CA (US); Oliver Peters, Bad Liebenzell (DE); Thomas Rocznik, Mountain View, CA (US)

(73) Assignee: Robert Bosch GmbH, Stuttgart (DE)

( * ) Notice: Subject to any disclaimer, the term of this patent is extended or adjusted under 35 U.S.C. 154(b) by 251 days.

(21) Appl. No.: 16/711,968

(22) Filed: Dec. 12, 2019

(65) Prior Publication Data
US 2020/0209178 A1 Jul. 2, 2020

Related U.S. Application Data

(60) Provisional application No. 62/787,071, filed on Dec. 31, 2018.

(51) Int. Cl.
*G01N 27/22* (2006.01)
*G01N 33/00* (2006.01)
*G01N 27/02* (2006.01)

(52) U.S. Cl.
CPC ............. *G01N 27/22* (2013.01); *G01N 27/02* (2013.01); *G01N 33/0098* (2013.01)

(58) Field of Classification Search
CPC ........ G01N 27/22; G01N 27/02; G01N 21/17; G01N 21/01; G01N 2021/0112; G01N 2021/1738; G01N 33/0098
See application file for complete search history.

(56) References Cited

U.S. PATENT DOCUMENTS

| 5,693,895 | A | 12/1997 | Baxter |
| 5,870,186 | A | 2/1999 | Mogan et al. |
| 6,858,403 | B2 | 2/2005 | Han et al. |
| 9,121,792 | B1 | 9/2015 | Agui et al. |
| 2004/0263331 | A1 | 12/2004 | Berndt |

(Continued)

FOREIGN PATENT DOCUMENTS

| CN | 101490539 A | 7/2009 |
| DE | 10148750 B4 | 12/2005 |

(Continued)

OTHER PUBLICATIONS

Goldfarb, Norman J., and Franz Herrmann. "A study of pH changes by molds in culture media." Journal of Investigative Dermatology 27.3 (1956): 193-201.

(Continued)

*Primary Examiner* — Amy He
(74) *Attorney, Agent, or Firm* — Brooks Kushman P.C.

(57) ABSTRACT

A mold sensor is configured with an enclosed chamber in which a nutrient-treated substrate is positioned. The mold sensor includes a sensor for measuring electrical properties of the substrate. The substrate includes conductive elements to interface with a controller to measure the electrical properties. The controller operates the sensor and is programmed to detect a presence of mold growing in the chamber based on the electrical properties.

17 Claims, 12 Drawing Sheets

(56) References Cited

U.S. PATENT DOCUMENTS

| | | |
|---|---|---|
| 2006/0146908 A1 | 7/2006 | Remsburg |
| 2009/0268201 A1 | 10/2009 | Call |
| 2012/0231492 A1 | 9/2012 | Bitterly et al. |
| 2013/0133404 A1 | 5/2013 | Patel et al. |
| 2014/0291548 A1 | 10/2014 | Basham et al. |
| 2016/0106873 A1 | 4/2016 | Dobrinsky et al. |
| 2018/0120865 A1 | 5/2018 | Nuryaningsih et al. |
| 2018/0340857 A1 * | 11/2018 | Roth ................. G08B 21/20 |
| 2020/0188180 A1 | 6/2020 | Akbari et al. |
| 2020/0209136 A1 | 7/2020 | Yee et al. |
| 2020/0209137 A1 | 7/2020 | Yee et al. |
| 2020/0209138 A1 | 7/2020 | Yee et al. |
| 2020/0209161 A1 | 7/2020 | Yee et al. |
| 2020/0209266 A1 | 7/2020 | Yee et al. |

FOREIGN PATENT DOCUMENTS

| | | | |
|---|---|---|---|
| EP | 2918993 A1 * | 9/2015 | ............ G01N 27/02 |
| EP | 2439513 B1 | 2/2018 | |
| JP | 2006192473 A | 7/2006 | |
| KR | 20130044437 A | 5/2013 | |

OTHER PUBLICATIONS

Papireddy Vinayaka, Poornachandra, et al. "An impedance-based mold sensor with on-chip optical reference." Sensors 16.10 (2016): 1603.

Savory, Eric, et al. "An optoelectronic sensor for the monitoring of mould growth in concealed spaces." Building and Environment 49 (2012): 9-16.

Viegas, Carla, and João Brandão. "Dispersion forms." Environmental Mycology in Public Health. Academic Press, 2016. 17-23.

Janczak, Daniel, et al. "Investigations of printed flexible pH sensing materials based on graphene platelets and submicron $RuO_2$ powders." Journal of Sensors 2017 (2017).

Korpi, Anne, Jill Jämberg, and Anna-Liisa Pasanen. "Microbial volatile organic compounds." Critical reviews in toxicology 39.2 (2009): 139-193.

Blank, Roland, et al. "Optical sensor system for the detection of mold: Concept for a fully automated sensor system for the detection of airborne fungal spores." 2015 IEEE Sensors. IEEE, 2015.

* cited by examiner

MOLD DETECTING DEVICE USING SENSOR TO MEASURE ELECTRICAL PROPERTIES

CROSS-REFERENCE TO RELATED APPLICATIONS

This application claims the benefit of U.S. provisional application Ser. No. 62/787,071 filed Dec. 31, 2018, the disclosure of which is hereby incorporated in its entirety by reference herein.

TECHNICAL FIELD

This application generally relates to an integrated sensor for detecting mold in an environment.

BACKGROUND

Mold can be a serious problem in many environments. Prolonged exposure to mold can cause health issues. Excessive mold growth can stain or degrade surfaces of a structure. Further, the presence of mold may be indicative of a moisture problem in the structure. Oftentimes, a mold problem may exist for some time without detection. In some cases, the mold growth is readily visible and can be detected by visual inspection. In many cases, mold is present but not readily visible to an observer. Ideally, it would be desirable to detect mold before it can cause health or structure issues.

Mold spreads by releasing spores in the air. The mold spores may grow when they land on a medium where conditions are suitable for growth. The conditions suitable for growth include appropriate levels of nutrients, water, and pH balance. Mold spores that do not land on such a medium may remain inactive and can be carried by air. Mold spores are found in most air in some concentration. Problem areas may have a higher concentration of mold spores.

A typical method of detecting mold is to collect a surface or air sample in an affected location. Particulate matter may be accumulated or placed on a microscope slide. An expert may view the slide through a microscope to identify mold and determine the mold concentration and types of mold that are present. These methods generally require taking the sample and sending the sample to a laboratory that has expertise in mold detection. Such processes tend to be labor intensive and rather expensive. Further, it can take some time to receive the results. The prior methods do not permit continuous sampling of an area.

SUMMARY

A mold detecting device includes a sensing device that is configured to measure one or more electrical properties of a growth surface. The growth surface includes a plurality of conductive contacts. In some configurations, the growth surface includes a grid of conductive contacts. In some configurations, the growth surface includes pairs of conductive strips. The mold detecting device includes an interface to electrically connect to the conductive strips. The mold detecting device is configured to apply a voltage across a pair of conductive strips or contacts. The mold detecting device is configured to measure an impedance across the conductive contacts that is changed by mold growth on the growth surface.

A mold sensor includes a housing defining a chamber and a substrate treated to promote mold growth and exposed within the chamber. The mold sensor includes a plurality of electrical contacts arranged on the substrate at predetermined intervals, wherein mold growth on the substrate affects electrical properties between the electrical contacts. The mold sensor includes a controller programmed to apply a voltage across pairs of the electrical contacts and measure a current passing through the electrical contacts, and output a signal indicative of mold growth on the substrate based on a change in the electrical properties derived from the voltage and the current.

The voltage may be an alternating current (AC) voltage. The controller may be further programmed to sweep a frequency and magnitude of the voltage. The controller may be further programmed to estimate a capacitance between the electrical contacts based on the voltage and the current and generate the signal responsive to changes in the capacitance. The electrical contacts may be arranged in a grid pattern on the substrate. The substrate may be divided into a plurality of regions and each of the regions may be treated with nutrients for growing different types of mold. The electrical contacts may be arranged as generally parallel conductive strips on the substrate. The mold sensor may further include one or more rollers configured to move the substrate into and out of the chamber and wherein the rollers include conductive contacts about a circumference of the rollers that interact with the electrical contacts to establish an electrical connection between the controller and the electrical contacts. The mold sensor may further include electrodes mounted to a frame below the substrate and the electrodes may include a compliant mechanism to bias the electrodes to contact the electrical contacts of the substrate. The mold sensor may further include one or more magnets mounted to a frame below the substrate and configured to interact with the electrical contacts to attract the substrate. The controller may be further programmed to measure a baseline impedance characteristic before mold growth and generate the signal based on differences between an impedance measurement and the baseline impedance characteristic.

A growth surface for a mold sensor includes a substrate treated with nutrients to promote mold growth and a plurality of electrical contacts attached to the substrate at predetermined positions, wherein mold growth on the substrate affects electrical properties between the electrical contacts.

The electrical contacts may be arranged in a grid pattern on the substrate. The substrate may be divided into a plurality of regions and each of the regions may be treated with nutrients for growing different types of mold. The electrical contacts may be arranged as generally parallel conductive strips on the substrate. The substrate may further includes gaps in the conductive strips at predetermined intervals corresponding to a size of a chamber in which the substrate is housed.

A method includes applying, by a controller, a voltage across a pair of electrical contacts attached to a nutrient-treated substrate within a chamber defined by a housing. The method includes receiving, by the controller, an electrical signal indicative of a current flowing through the electrical contacts from a current sensor. The method includes outputting, by the controller, a signal based on an electrical characteristic derived from the voltage and the current being indicative of mold growth on the nutrient-treated substrate.

The voltage may be an alternating current (AC) voltage. The method may further include sweeping a frequency and a magnitude of the voltage over predetermined ranges. The method may further include measuring a baseline electrical characteristic prior to mold growth, and generating the signal based on a difference between the electrical characteristic and the baseline electrical characteristic.

DETAILED DESCRIPTION

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

An improved way of detecting mold may be an integrated sensor device that can detect the presence of mold without having to send a sample to a laboratory. A further advantage of an integrated sensor is that the mold sensor may be placed in a location to continuously monitor the location. This can generate an alert when mold becomes a problem. A mold sensor is disclosed herein that is configured to sample air and detect a concentration of mold in the air. The mold sensor may be configured to create a small enclosed environment that is conducive to mold growth. Mold growth may be detected in a variety of ways.

This application first discloses general configurations and structural elements for a mold sensing device. Specific mold sensing technologies and strategies are then disclosed that are applicable to the general configurations. Various operating modes and strategies are then disclosed. A mold sensing system may incorporate a plurality of mold sensors. The mold sensor may be of a common design with communication capability. The mold sensing system may include a reference mold sensor and a target area mold sensor. The reference mold sensor may provide mold concentration information that is expected in the environment (e.g., outdoors). The target mold sensor may provide mold concentration information for an area of interest (e.g., basement, living space). The mold sensing system may incorporate results from multiple sensors to accurately determine mold concentrations in the target area.

Figure 1:
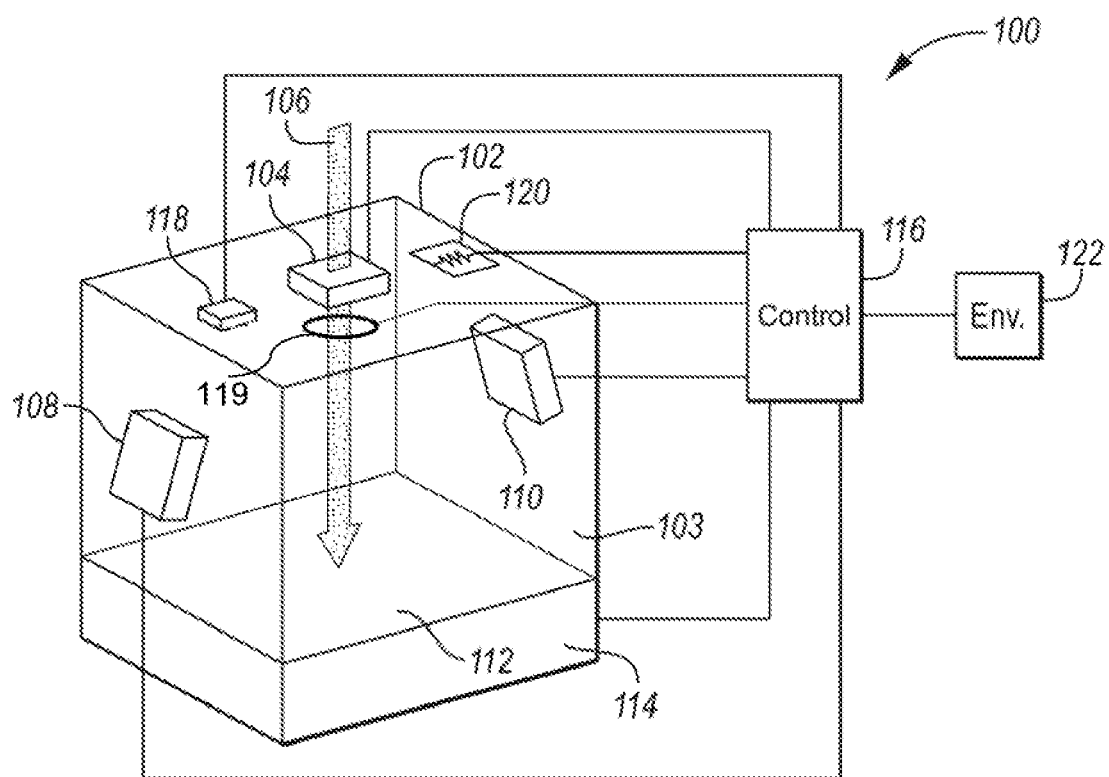
FIG. 1 depicts a single chamber mold sensor configuration with an integrated sensor module.

FIG. 1 depicts a diagram of a configuration for a first mold sensor configuration 100. The first mold sensor configuration 100 may include a housing 102 that defines a chamber 103. The housing 102 may define a bottom opening to allow a surface to be exposed within the chamber 103 (e.g., housing 102 has no bottom). The housing 102 may be constructed from plastic, metal, and/or other suitable materials that do not outgas or are otherwise not conducive to mold/bacteria growth. Surfaces of the housing 102 that are within the chamber 103 may be coated with a layer to avoid or inhibit mold growth (e.g., alkaline coating with pH>7). While shown as a cube, the shape of the housing 102 may be otherwise shaped. The specific shape of the housing 102 may be dependent on other mechanisms that are coupled to the housing 102.

The first mold sensor configuration 100 may include an air entry portal 104. The air entry portal 104 may be configured to define an airflow path 106 into the chamber 103. In some configurations, the housing 102 may define an opening to act as the air entry portal 104. In some configurations, the air entry portal 104 may be configured to selectively open and close. For example, a movable grate or door may be placed over an opening defined by the housing 102. The movable grate or door may be electrically actuated by a solenoid into an open or closed position. A spring mechanism may hold the movable grate in a normally closed position. The solenoid may be actuated by a control device 116. The movable grate or door may be electrically, magnetically, or mechanically operated. Some configurations may include an airflow sensor 119 to determine airflow into the chamber 103. The airflow sensor 119 may be electrically coupled to the control device 116. While not shown in all configurations, the airflow sensor 119 may be incorporated into the other configurations that are described herein.

The control device 116 may be a controller that includes a processing unit and non-volatile and volatile memory. The controller may be programmed to perform various operations related to operating the mold sensor. The control device 116 may further include any electrical interfaces for interacting with actuators and sensors that are part of the mold sensor. In addition, the control device 116 may include a network interface for accessing networks. The network interface may be wired and/or wireless. The network interface may provide a communication path for accessing the Internet/world-wide web. The control device 116 may be mounted to the housing 102.

The first mold sensor configuration 100 may further include a growth surface 112. The growth surface 112 may be a surface that is exposed within the chamber 103 and that is suitable for mold growth. In some configurations, the growth surface 112 may be exposed to air outside of the chamber 103. For example, the growth surface 112 may be exposed to the environment outside of the chamber 103 for air sampling, followed by moving the growth surface 112 into the chamber 103 for mold growth. The air entry portal 104 may be configured to define the airflow path 106 such that air is directed to flow toward the growth surface 112. The growth surface 112 may be configured as a surface that is conducive to capturing mold spores from the air. The growth surface 112 may be configured as a medium suitable to promote mold growth. The growth surface 112 may be treated with nutrients that promote mold growth. For example, nutrients may include organic materials, salt, agar, and/or sugar. The growth surface 112 may also be configured to supply a sufficient moisture content to encourage mold growth or may be packaged in a manner to retain the moisture content until usage. The growth surface 112 may include anti-bacterial chemicals or treatments to prevent bacteria from growing. The growth surface 112 may be a tape, a membrane, or a filter. The tape, membrane, or filter may be treated with various substances to promote mold growth. The tape, membrane, or filter may be air-permeable or non-permeable. One or more temperature and humidity/moisture sensors may be integrated with the growth surface 112 to allow monitoring of the mold growth environment.

The specific conditions for promoting mold growth may depend on the type of mold to be grown. Different molds may prefer a different nutrient environment. The growth surface 112 may further includes regions (e.g., stripes) that are configured to grow different types of mold. For example, each region of the growth surface 112 may be treated with a different nutrient mixture that promotes the growth of a different type of mold. An advantage of this configuration is that the types of mold present may be identified by monitoring mold growth in each of the regions.

The first mold sensor configuration 100 may include a sensing device 110 that is configured to sense mold growing on the growth surface. The placement of the sensing device 110 may be dependent on the type of sensing that is performed. Further, the orientation of the sensing device 110 relative to the housing 102 may depend on the type of sensing device 110. For example, FIG. 1 depicts the sensing device 110 mounted at an angle relative to the housing 102. Some sensing device configurations may perform better when directed toward or through the growth surface 112. A variety of technologies are available for the sensing device 110. The sensing device 110 may be electrically connected to the control device 116. The sensing device 110 may be contained within a single module that is coupled to the housing 102. Some sensor configurations (e.g., optical or audio) may utilize a source module and a receiver module. The sensing device 110 may integrate the source and receiver modules into a single unit. In some configurations, the sensing device 110 may include multiple sensing devices of the same or different technology that are placed in different positions within the housing 102. Various configurations of the sensing device 110 are disclosed herein.

The first mold sensor configuration 100 may include a mold suppressor 108 that is configured to destroy mold. The mold suppressor 108 may be mounted on a side of the housing 102. For example, the mold suppressor 108 may be one or more ultraviolet (UV) light sources. For example, the mold suppressor 108 may be a single UV light source or an array of UV light sources. The UV light source may be a source illuminating divergent beam that can illuminate the entire growth surface 112 that is exposed in the chamber 103. The UV light source may be a UV source with a beam divergence component to enlarge the UV beam to illuminate the entire growth surface 112 that is exposed in the chamber 103. The mold suppressor 108 may be a UV light source with a driver to sweep the UV light source across the growth surface 112 that is exposed within the chamber. In addition, the mold suppressor 108 may be configured to destroy mold on other surfaces of the chamber 103 (e.g., inner-side walls) and the air entry port 104. The mold suppressor 108 may be electrically actuated by the control device 116. The mold suppressor 108 may be actuated for a predetermined period of time to destroy mold that has grown. The control device 116 may activate the mold suppressor 108 after completion of a measurement cycle to destroy mold that was grown during the measurement cycle. The mold suppressor 108 may be operated to destroy mold within the chamber 103 to define a baseline condition before starting a measurement cycle.

The first mold sensor configuration 100 may further include a surface exchange mechanism 114 that is configured to support the growth surface 112 and facilitate exchange of the growth surface 112. In some configurations, the growth surface 112 may be fixed to the surface exchange mechanism 114. The surface exchange mechanism 114 may be configured to selectively couple to the housing 102. After a measurement cycle is completed, the growth surface 112 may be replaced to enable another measurement cycle. The surface exchange mechanism 114 may be attached to and detached from the housing 102 to change the growth surface 112 when desired. The housing 102 may define an opening on a bottom surface to expose the growth surface 112 to the chamber 103 when the surface exchange mechanism 114 is coupled to the housing 102. In some configurations, the housing 102 may be constructed without a bottom surface.

In some configurations, the growth surface 112 may be movable and the surface exchange mechanism 114 may be configured to move the growth surface 112 to another position. The surface exchange mechanism 114 may be configured to store portions of the growth surface 112 that are not currently exposed within the housing 102. The portions stored may include an unused portion and a used portion. The surface exchange mechanism 114 may be configured to be electrically/mechanically actuated and may be electrically coupled to the control device 116. Various configurations of the surface exchange mechanism 114 are discussed in more detail in subsequent sections herein. In some configurations, the surface exchange mechanism 114 may include the capability to electrostatically charge the growth surface 112 to improve the ability to attract mold spores.

The first mold sensor configuration 100 may include one or more thermal control elements 120 that are configured to change the temperature in the chamber 103 to promote mold growth. Additional thermal control elements may be embedded on, in, or below the growth surface 112. The thermal control element 120 may be electrically coupled to the control device 116. The thermal control element 120 may include a thermoelectric cooling element. For example, the thermal control element 120 may be a thermoelectric heat pump (e.g., Peltier device or heat pump). The thermal control element 120 may include a heating element such as a resistive element. The thermal control element 120 may include an infrared source (IR). The thermal control element 120 may be a single element or may be comprised of a plurality of thermal control elements positioned at different locations in the chamber 103 to independently control the temperature in different areas of the chamber 103. In some configurations, the mold sensor may include a mechanism for adjusting humidity within the chamber 103. Different environmental conditions (e.g., temperature) within the same nutrient zone may be used to distinguish between different types of mold. For example, a given nutrient zone exposed to different environmental conditions may create multiple zones that favor growth of different types of mold. The thermal control element 120 may be configured to create different temperature conditions in different regions of the growth surface 112. For example, by placing the thermal control element 120 on one side of the chamber 103, temperatures may increase or decrease as the distance from the thermal control element 120 increases. This may provide different environmental conditions for different parts of the growth surface 112.

The first mold sensor configuration 100 may include a chamber environment sensor 118 that is configured to measure environmental conditions within the chamber 103. The chamber environment sensor 118 may be electrically connected to the control device 116. The chamber environment sensor 118 may include one or more temperature sensors, a humidity sensor a pressure sensor and/or a gas sensor. A temperature sensor may be positioned in a path of the airflow that enters the chamber 103. The chamber environment sensor 118 may be monitored at periodic intervals to determine the status of conditions within the chamber 103.

An external environment sensing module 122 may be present to provide information about the environment external to the chamber 103. The environmental sensing module 122 may include a temperature sensor, humidity sensor, pressure sensor, and/or gas sensor. The environmental sensing module 122 may be electrically coupled to the control device 116. The external environment sensing module 122 may be integrated with the housing 102 or may be a separate module that communicates with the control device 116. Communication between the control device 116 and the external environment sensing module 122 may be via a wireless communication protocol (e.g., Bluetooth, Bluetooth LE, WiFi, optical). The environmental sensing module 122 may provide information on conditions surrounding or nearby the first mold sensor configuration 100 that may influence mold growth. The control device 116 may be further configured to receive information from an external network (e.g., Internet) to provide additional context for mold detection. The presence and/or concentration of mold spores may vary depending on time of day, season, and environmental parameters. The control device 116 may collect this additional information and utilize the information in the mold detection process. The control device 116 may use the information to determine the conditions for initiating a measurement cycle. For example, during times of the year when mold spores are present in higher concentrations, the control device 116 may initiate measurement cycles more often.

Figure 2:
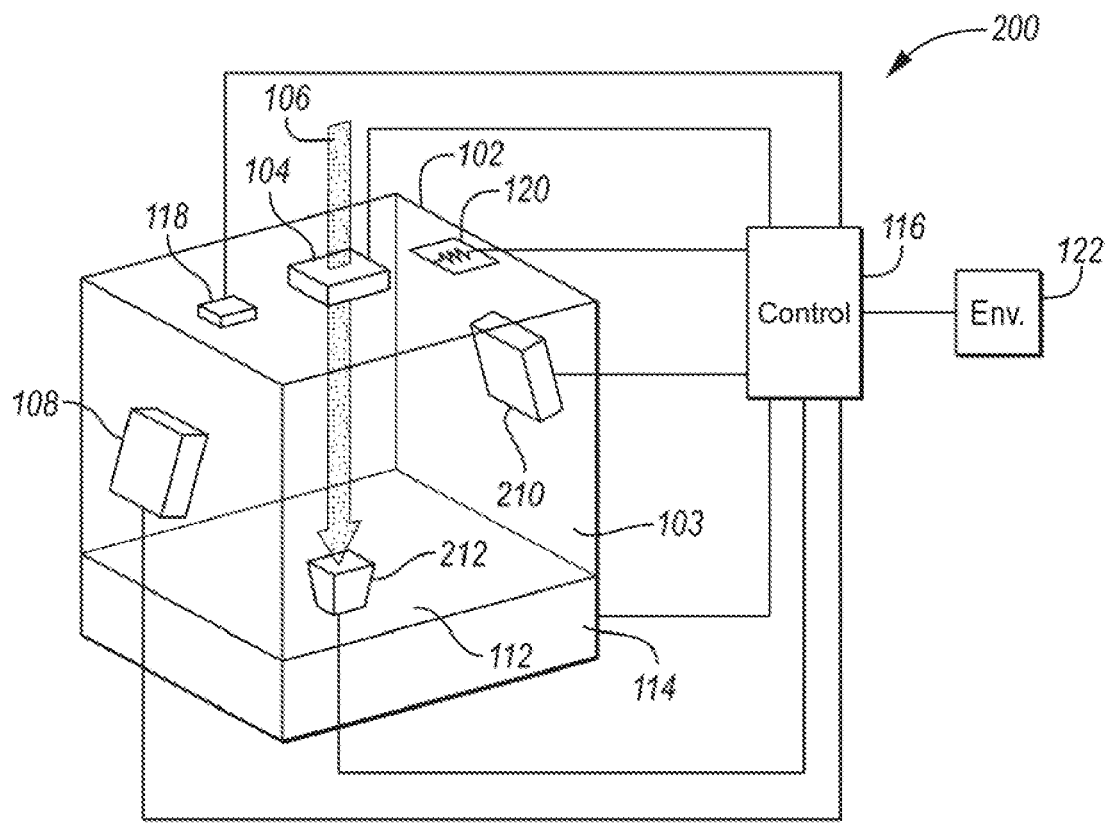
FIG. 2 depicts a single chamber mold sensor configuration with a multi-piece sensor.

FIG. 2 depicts a second mold sensor configuration 200. The second mold sensor configuration 200 may be configured for sensors in which the source and receiving modules are not integrated. The second mold sensor configuration 200 may include a sensor source module 210 and a sensor receiving module 212. For example, in an optical sensing system, the sensor source module 210 may be a light source and the sensor receiving module 212 may be light sensor. The sending and receiving modules may operate cooperatively to detect mold within the chamber 103. The sensor source module 210 and the sensor receiving module 212 may be electrically coupled to the control device 116. In operation, the control device 116 may activate the sensor source module 210 and receive signals from the sensor receiving module 212.

In the configuration depicted, the sensor source module 210 is coupled to a side wall of the housing 102. The sensor receiving module 212 is coupled beneath the growth surface 112. The sensor receiving module 212 may be mounted to a frame or platform that is beneath the growth surface 112. The sensor source module 210 and the sensor receiving module 212 may be aligned to ensure that the sensor receiving module 212 can receive signals from the sensor source module 210. In other configurations, the positions of the sensor receiving module 212 and the sensor source module 210 may be reversed.

The first mold sensor configuration 100 may be described as having an integrated mold sensing device. That is, the sensing device 110 is a single module that is coupled to the housing 102. The second mold sensor configuration 200 may be described as having a two-part sensing device. The second mold sensor configuration 200 may be useful for sensing configurations that measure a characteristic that is transmitted through the growth surface 112.

The air entry port 104, mold suppressor 108, sensing device(s), thermal control element 120, and chamber environment sensor 118 may be mounted in various configurations. The particular location selected may depend on packaging constraints of the housing and/or performance considerations for mold detection. The location of the sensing device(s) may be selected depending on the type of sensing device being used. For example, a sensing device using optical sensors may be positioned differently than a sensing device configured to measure electrical properties.

Figure 3:
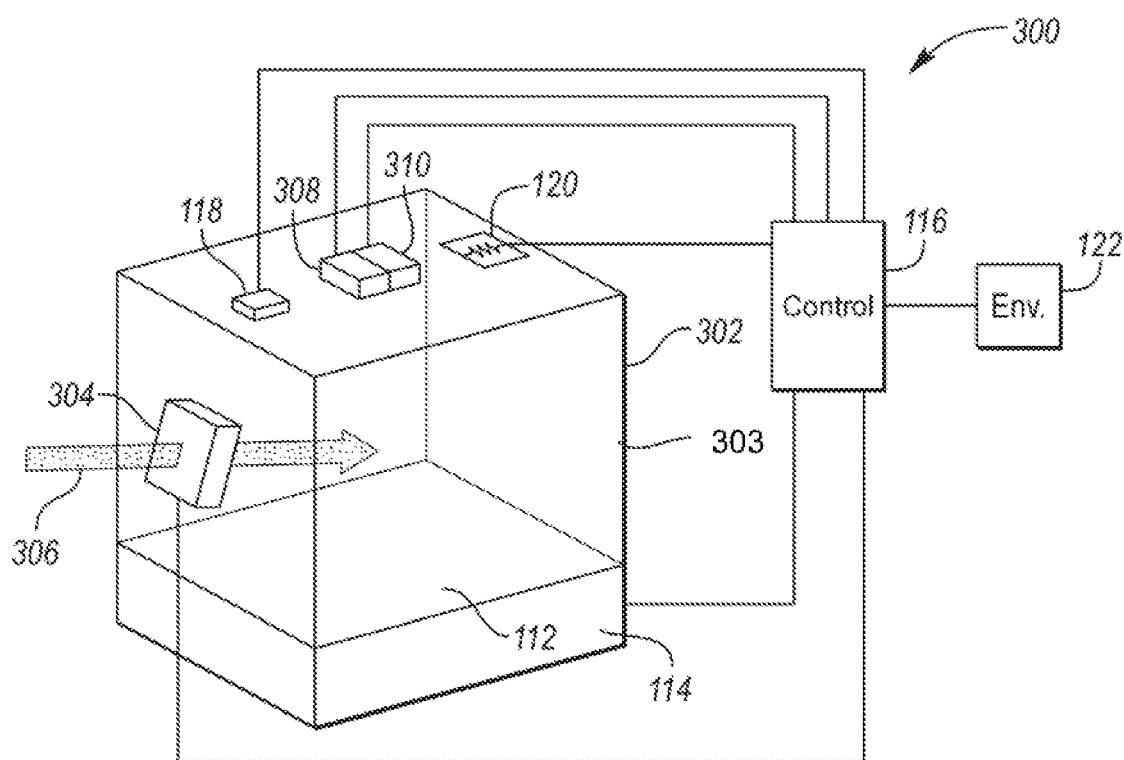
FIG. 3 depicts an alternative configuration of a single chamber mold sensor with an integrated sensor.

FIG. 3 depicts a third mold sensor configuration 300. The third mold sensor configuration 300 may include a housing 302 that defines a chamber 303. The third mold sensor configuration 300 may include a side air entry portal 304. The side air entry portal 304 may be configured to create an airflow path 306 into the chamber 303. In some configurations, the side air entry portal 304 may redirect the flow of air to divert airflow toward the growth surface 112. For example, the side air entry portal 304 may include angled slats or strips to redirect air flow. In some configurations, the housing 302 may define an opening to act as the side air entry portal 304. In some configurations, the side air entry portal 304 may be configured to selectively open and close. For example, a movable grate or door may be placed over an opening defined by the housing 302. The movable grate or door may be electrically actuated by a solenoid into an open or closed position. A spring mechanism may hold the movable grate in a normally closed position. The solenoid may be actuated by the control device 116. The movable grate or door may be electrically, magnetically, or mechanically operated.

The third mold sensor configuration 300 may include a top-mounted mold suppressor 308. The top-mounted mold suppressor 308 may function as described previously with reference to the mold suppressor 108 of FIG. 1. The third mold sensor configuration 300 may include a top-mounted sensing device 310. The top-mounted sensing device 310 may function as described previously with reference to the sensing device 110 of FIG. 1. The top-mounted mold suppressor 308 and sensing device 310 may be integrated into a single unit (e.g., a sensor/suppressor module). An integrated device may facilitate assembly of the mold sensor.

The third mold sensor configuration 300 describes a configuration with different air entry ports and sensor locations. The components may generally function as previously described.

Figure 4:
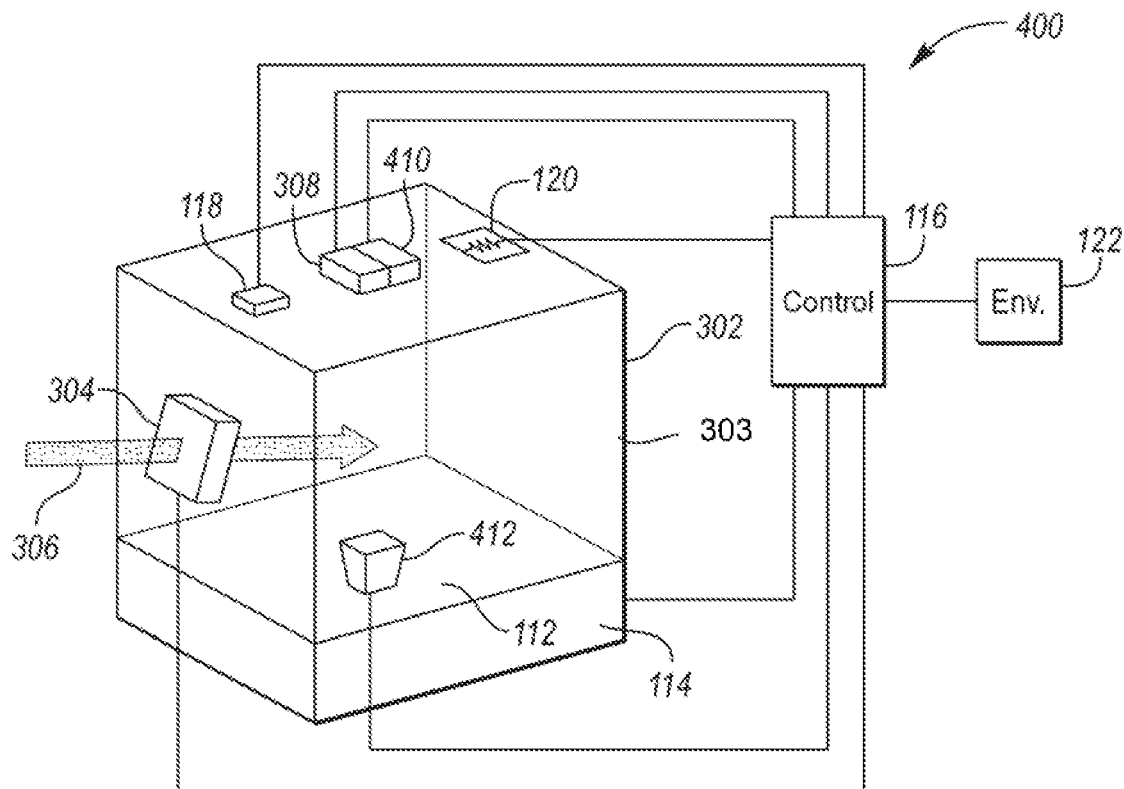
FIG. 4 depicts an alternative configuration of a single chamber mold sensor with a multi-piece sensor.

FIG. 4 depicts a fourth mold sensor configuration 400. The fourth mold sensor configuration 400 may be configured for sensors in which the source and receiving modules are not integrated. The fourth mold sensor configuration 400 may include a top-mounted sensor source module 410 and a sensor receiving module 412. For example, in an optical sensing system, the top-mounted sensor source module 410 may be a light source and the sensor receiving module 412 may be light sensor. The sending and receiving modules may operate cooperatively to detect the mold. The top-mounted sensor source module 410 and the sensor receiving module 412 may be electrically coupled to the control device 116. In operation, the control device 116 may activate the top-mounted sensor source module 410 and receive signals from the sensor receiving module 412.

In the configuration depicted, the top-mounted sensor source module 410 is coupled to a top wall or ceiling of the housing 302. The sensor receiving module 412 is coupled beneath the growth surface 112. The top-mounted sensor source module 410 and the sensor receiving module 412 may be aligned to ensure that the sensor receiving module 412 can receive signals from the top-mounted sensor source module 410. The top-mounted mold suppressor 308 and top mounted sensor source 410 may be integrated into a single unit (e.g., a sensor source/suppressor module). An integrated device may facilitate assembly of the mold sensor. In other configurations, the positions of the sensor source module 410 and the sensor receiving module 412 may be reversed.

Figure 5:
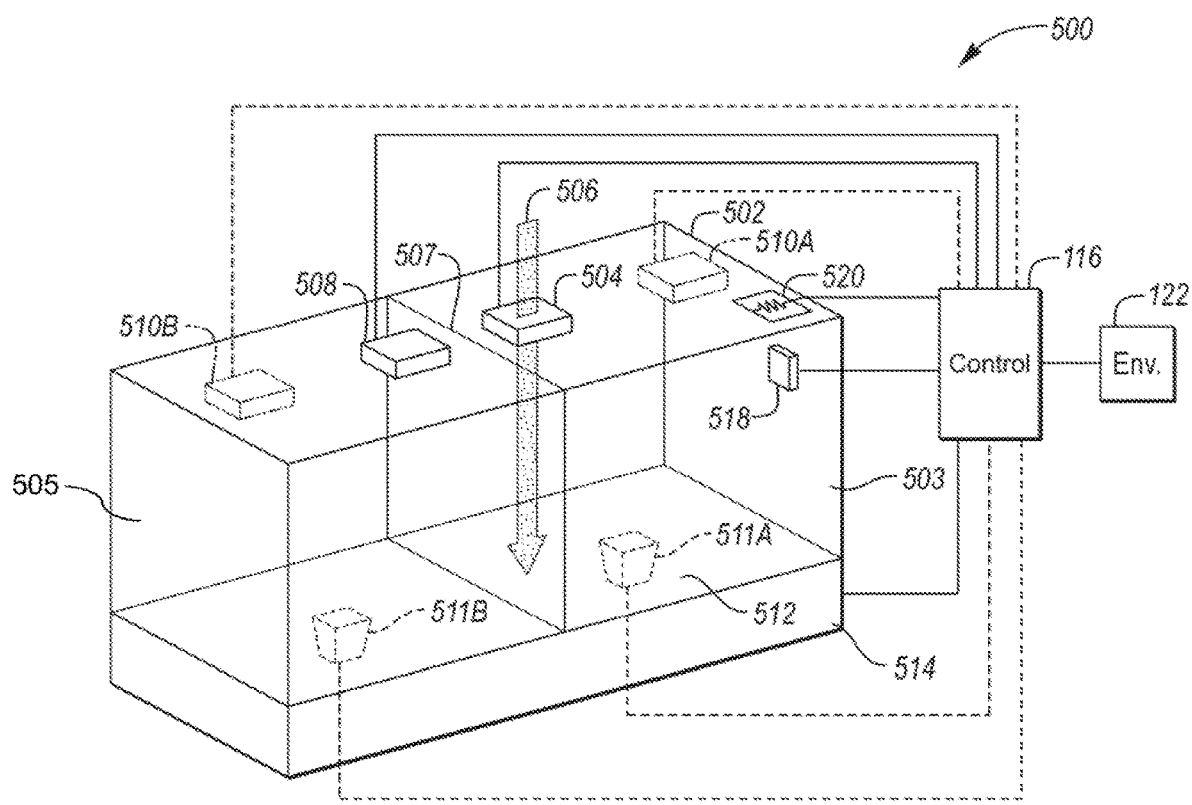
FIG. 5 depicts an example of a multi-chamber mold sensor configuration.

FIG. 5 depicts a dual-chamber mold sensor configuration 500. The dual-chamber mold sensor configuration 500 may include a dual-chamber housing 502 that includes a dividing wall 507 that defines a first chamber 503 and a second chamber 505. The first chamber 503 may be used for growing mold on a portion of a growth surface 512 that is exposed within the first chamber 503.

The dual-chamber mold sensor configuration 500 may include an air entry portal 504. The air entry portal 504 may be configured to define an airflow path 506 into the first chamber 503. In some configurations, the dual-chamber housing 502 may define an opening to act as the air entry portal 504. In some configurations, the air entry portal 504 may be configured to selectively open and close. For example, a movable grate or door may be placed over an opening defined by the dual-chamber housing 502. The movable grate or door may be electrically actuated by a solenoid into an open or closed position. A spring mechanism may hold the movable grate in a normally closed position. The solenoid may be actuated by a control device 116. The movable grate or door may be electrically, magnetically, or mechanically operated.

The dual-chamber mold sensor configuration 500 may include one or more mold sensing devices 510 that are configured to sense mold growing on the growth surface 512. The placement of the sensing device 510 may be dependent on the type of sensing that is performed. A variety of technologies are available for the sensing device 510. The sensing device 510 may be electrically connected to the control device 116. The sensing device 510 may be contained within a single module that is coupled to the housing 502. Various configurations of the sensing device 510 are disclosed herein.

The dual-chamber mold sensor configuration 500 may include one or more sensor receiving modules 511. The sensor receiving modules 511 may be present in configurations in which the sensing device 510 acts as a source. The dual-chamber mold sensor configuration 500 may be configured to have a single mold sensing device 510A configured to detect mold growth in the first chamber 503. The dual-chamber mold sensor configuration 500 may be configured to have a single mold sensing device 510A and a single sensor receiving module 511A configured to detect mold growth in the first chamber 503. The dual-chamber mold sensor configuration 500 may be configured to have a single mold sensing device 510B configured to detect mold growth in the second chamber 505. The dual-chamber mold sensor configuration 500 may be configured to have a single mold sensing device 510B and a single sensor receiving module 511B configured to detect mold growth in the second chamber 505. The dual-chamber mold sensor configuration 500 may also be configured to have mold sensing devices 510A/511A, 510B/511B in both the first chamber 503 and the second chamber 505.

The dual-chamber mold sensor configuration 500 may include a mold suppressor 508 that is configured to destroy mold. The mold suppressor 508 may be mounted on a side or top of the housing 502. The mold suppressor 508 may be configured to destroy mold in the second chamber 505. The mold suppressor 508 may function as previously described herein. Further, the mold suppressor 508 may be integrated with the mold sensing device 510 as previously described herein.

The dual-chamber mold sensor configuration 500 may further include a surface exchange mechanism 514 that is configured to move the growth surface 512 to another position. For example, the surface exchange mechanism 514 may include one or more rollers that are configured to move the growth surface 512. The growth surface 512 that is exposed within the first chamber 503 may be referred to as an active growth surface. The active growth surface may be the surface on which mold is to be grown or is growing. The portion of the growth surface 512 that is exposed within the second chamber 505 may be referred to as the used surface. The used surface may the surface on which mold has already been grown. The surface exchange mechanism 514 may be configured to advance the growth surface 512 to provide a new active growth surface within the first chamber 503. The surface exchange mechanism 514 will be described in more detail herein. Another configuration may be in which the growth surface 512 is exposed to air in the first chamber 503 and then moved to the second chamber 505 for growth, measurement, and destruction (e.g., similar to single chamber configurations).

The dual-chamber mold sensor configuration 500 may include a thermal control element 520 that is configured to change the temperature in the first chamber 503 to promote mold growth. Additional thermal control elements may be embedded on, in, or below the growth surface 512. The thermal control element 520 may be a thermoelectric element that is electrically driven by the control device 116. The dual-chamber mold sensor configuration 500 may also include a similar thermal control element in the second chamber 505. The thermal control element 520 may function as described previously for the similar element of the other configurations.

The dual-chamber mold sensor configuration 500 may include a chamber environment sensor 518 that is configured to measure environmental conditions within the first chamber 503. The chamber environment sensor 518 may be electrically connected to the control device 116. The chamber environment sensor 518 may include a temperature sensor, a humidity sensor, a pressure sensor, and/or a gas sensor. The chamber environment sensor 518 may be monitored at periodic intervals to determine the status of conditions within the first chamber 503. The dual-chamber mold sensor configuration 500 may also include a similar environment sensor in the second chamber 505.

The dual-chamber mold sensor configuration 500 provides separate chambers for mold growth and destruction. An advantage of the dual-chamber mold sensor configuration 500 is that the sensor can be continually used for mold sensing. The single chamber configurations grow and destroy mold in the same chamber so that during the mold destruction phase a new sample may not be initiated. In some configurations, the mold sensor may utilize more than two chambers. A multi-chamber mold sensor configuration may also be used. For example, different chambers may be configured to be operated to different environmental parameters to create a growth environment for different types of mold.

The general operation of the dual-chamber mold sensor configuration 500 may be to expose a portion of the growth surface 512 in the first chamber 503. The air entry portal 504 may be opened at a predetermined time for a predetermined amount of time and then closed. The control device 116 may operate the thermal control element 520 and monitor the chamber environment sensors 518 to produce an environment conducive to mold growth. The control device 116 may monitor signals from the sensing device 510/511 to determine if mold is present. Upon completion of the measurement cycle, the control device 116 may activate the surface exchange mechanism 514 to move the growth surface 512 such that the exposed portion in the first chamber 503 moves to the second chamber 505. A new active growth surface may be moved into the first chamber 503 to enable a new measurement cycle.

The control device 116 may then operate the mold suppressor 508 to destroy the mold on the growth surface 512. In configurations with a mold sensing device (e.g., 510B/511B) in the second chamber 505, the control device 116 may monitor the corresponding signals for signs of mold destruction.

Figure 6:
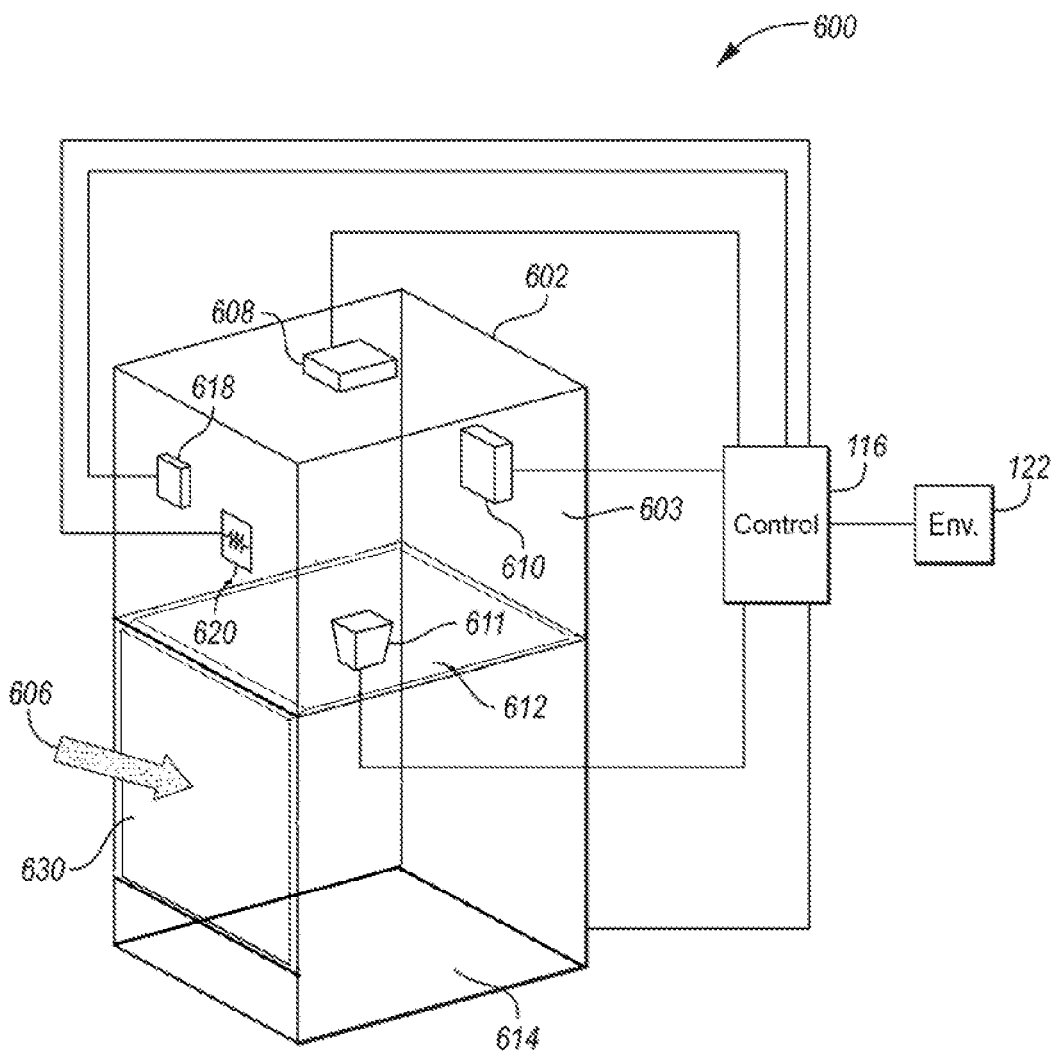
FIG. 6 depicts an example of a single chamber mold sensor configured to expose a surface to airflow outside of the single chamber.

FIG. 6 depicts a first single-chamber with external exposure configuration 600. The single-chamber/external exposure configuration 600 may incorporate a single chamber that is configured to grow and destroy mold. The single-chamber/external exposure configuration 600 may include a housing 602 that defines a chamber 603. The single-chamber/external exposure configuration 600 further includes a growth surface 612. The growth surface 612 may be configured to be exposed to airflow 606 outside of the chamber 603.

The single-chamber/external exposure configuration 600 further includes a surface exchange mechanism 614 that is configured to move the growth surface 612 into different positions. An exposed portion 630 of the growth surface 612 may be exposed to airflow 606 outside of the chamber 603. The exposed portion 630 may be subjected to airflow 606 for a predetermined amount of time to collect mold spores that are present in the airflow 606. The surface exchange mechanism 614 may be actuated to move the exposed portion 630 into the chamber 603. As such, an additional previously unexposed portion of the growth surface 612 may be positioned to be the exposed portion 630. The surface exchange mechanism 614 is described in additional detail herein.

The single-chamber/external exposure configuration 600 may include a mold sensing device 610 that is configured to sense mold growing on the growth surface 612. The placement of the sensing device 610 may be dependent on the type of sensing that is performed. A variety of technologies are available for the sensing device 610. The sensing device 610 may be electrically connected to the control device 116. The sensing device 610 may be contained within a single module that is coupled to the housing 602. Various configurations of the sensing device 610 are disclosed herein. The single-chamber/external exposure configuration 600 may include a sensor receiving module 611. The sensor receiving module 611 may be present in configurations in which the sensing device 610 is configured as a source. The sensor receiving module 611 may be positioned below the portion of the growth surface 612 that is within the chamber 603.

The single-chamber/external exposure configuration 600 may include a mold suppressor 608 that is configured to destroy mold in the chamber 603. The mold suppressor 608 may be mounted on a side or top of the housing 602 (depicted on top). The mold suppressor 608 may function as previously described herein. Further, the mold suppressor 608 may be integrated with at least a portion of the mold sensing device 610 as previously described herein.

The first single-chamber/external exposure configuration 600 may include a thermal control element 620 that is configured to change the temperature in the chamber 603 to promote mold growth. Additional thermal control elements may also be embedded on, in, or below the growth surface 612. The thermal control element 620 may be a thermoelectric element that is electrically driven by the control device 116. The single-chamber/external exposure configuration 600 may include a chamber environment sensor 618 that is configured to measure environmental conditions within the chamber. The thermal control element 620 may operate as described herein.

The first single-chamber with external exposure configuration 600 is characterized in part by the trajectory of the growth surface 612. As depicted, the growth surface 612 within the chamber 603 is oriented at an angle of ninety degrees in relation to the exposed growth surface 630. The angle is not limited to ninety degrees. The first single-chamber with external exposure configuration 600 allows a mold measurement to take place while another air sample is being exposed to the airflow 606.

Figure 7:
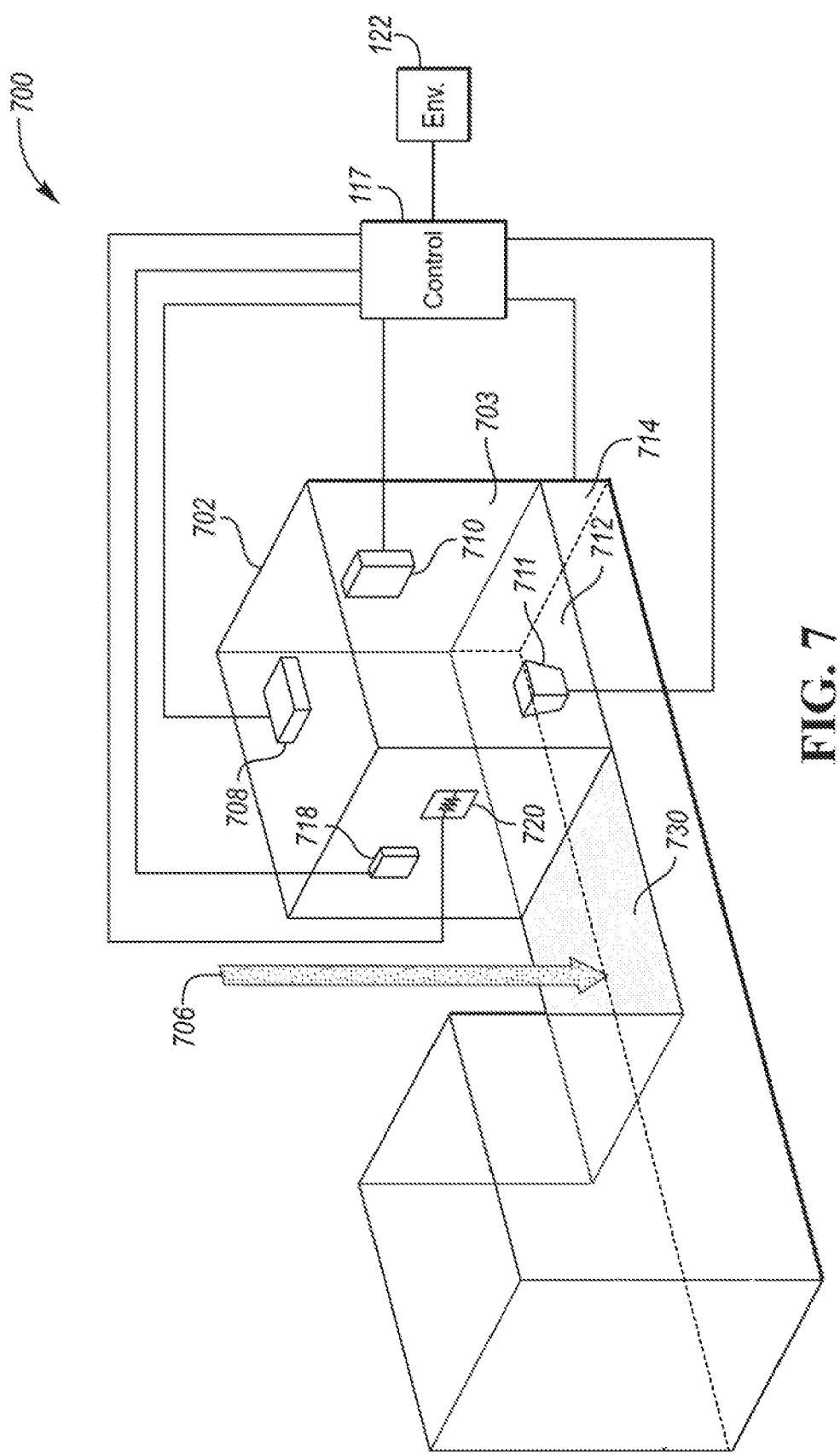
FIG. 7 depicts a second example of a single chamber mold sensor configured to expose a surface to airflow outside of the single chamber.

FIG. 7 depicts a second single-chamber with external exposure configuration 700. The single-chamber/external exposure configuration 700 may incorporate a single chamber that is configured to grow and destroy mold. The single-chamber/external exposure configuration 700 may include a housing 702 that defines a chamber 703. The single-chamber/external exposure configuration 700 further includes a movable growth surface 712. The movable growth surface 712 may be configured to be exposed to airflow 706 outside of the chamber 703.

The single-chamber/external exposure configuration 700 further includes a surface exchange mechanism 714 that is configured to move the growth surface 712 into different positions. An exposed portion 730 of the growth surface 712 may be exposed to airflow 706. The exposed portion 730 may be subjected to airflow 706 for a predetermined amount of time to collect mold spores that are present in the airflow 706. The surface exchange mechanism 714 may be actuated to move the exposed portion 730 into the chamber 703. As such, another portion of the growth surface 712 may be positioned to be the exposed portion 730. The surface exchange mechanism 714 is described in additional detail herein.

The single-chamber/external exposure configuration 700 may include a mold sensing device 710 that is configured to sense mold growing on the growth surface 712. The placement of the sensing device 710 may be dependent on the type of sensing that is performed. A variety of technologies are available for the sensing device 710. The sensing device 710 may be electrically connected to the control device 116. The sensing device 710 may be contained within a single module that is coupled to the housing 702. Various configurations of the sensing device 710 are disclosed herein. The single-chamber/external exposure configuration 700 may include a sensor receiving module 711. The sensor receiving module 711 may be present in configurations in which the sensing device 710 acts as a source. The sensor receiving module 711 may be positioned below the growth surface 712 that is within the chamber 703.

The single-chamber/external exposure configuration 700 may include a mold suppressor 708 that is configured to destroy mold. The mold suppressor 708 may be mounted on a side or top of the housing 702 (depicted on top). The mold suppressor 708 may be configured to destroy mold in the chamber 703. The mold suppressor 708 may function as previously described herein. Further, the mold suppressor 708 may be integrated with at least a portion of the mold sensing device 710 as previously described herein.

The first single-chamber/external exposure configuration 700 may include a thermal control element 720 that is configured to change the temperature in the chamber 703 to promote mold growth. Additional thermal control elements may be embedded on, in, or below the growth surface 712. The thermal control element 720 may be a thermoelectric element that is electrically driven by the control device 117. The single-chamber/external exposure configuration 700 may include a chamber environment sensor 718 that is configured to measure environmental conditions within the chamber.

The second single-chamber with external exposure configuration 700 may be characterized in part by the trajectory of the growth surface 712. As depicted, the growth surface 712 within the chamber 703 is oriented in the same plane in relation to the exposed growth surface 730. The second single-chamber with external exposure configuration 700 may be mounted at any angle relative to the airflow 706. The sensor may be mounted so that air impacts the exposed growth surface 730 at a predetermined angle.

The mold sensor configurations disclosed herein may utilize a surface exchange mechanism that is configured to exchange a portion of the growth surface that is within the detection chamber. In addition, the surface exchange mechanism may be configured to move an exposed growth surface into the detection chamber. The growth surface or medium may be configured in a variety of ways. The growth medium may be a film or tape that is coated to create a sticky or tacky surface. The sticky surface aids in attracting particles such as mold spores. In addition, the surface of the film or tape may be coated with nutrients for mold growth. The surface of the film or tape may be coated with an antibacterial coating to prevent bacteria growth.

Figure 8:
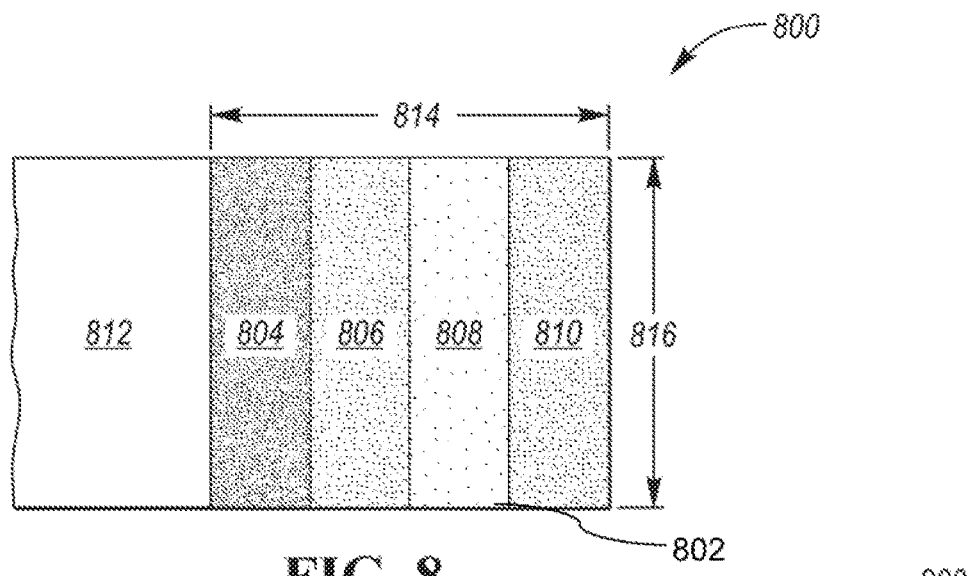
FIG. 8 depicts a growth surface including stripes of different nutrient treatments.

Different types of mold may favor different nutrients for growth. The growth medium may be configured to encourage different types of mold to grow. FIG. 8 depicts a possible configuration of a growth medium 800. The growth medium 800 may include a substrate material 812. For example, the substrate material 812 may be a film, membrane, or tape. The substrate material 812 may be made of plastic, fabric or other material. In various configurations, the substrate material 812 may be formed as a strip, a drum, or a disc. A plurality of test sections 802 may be defined on the substrate material 812. The test section 802 may be defined as an area or surface of the growth medium 800 that can be exposed within the chamber of the mold sensor. The test sections 802 may be characterized by a width 816 and a length 814. The width 816 and length 814 may correspond to the dimensions of the chamber or dimensions of an opening for exposing the test section 802 within the chamber. The test section 802 may be repeated continuously on the substrate material 812. During operation of the mold sensor, the test section 802 may be exposed to air and processed through a measurement cycle. The remaining test sections defined on the substrate material 812 may be enclosed by the surface exchange mechanism.

The test section 802 may be segmented into a plurality of stripes. For example, a first stripe 804, a second stripe 806, a third stripe 808, and a fourth stripe 810 may be defined on the test section 802. Each of the stripes may have a coating that favors the growth of a different type of mold. For example, the first stripe 804 may include a first nutrient coating favorable for growing a first mold type. The second stripe 806 may include a second nutrient coating favorable for growing a second mold type. The third stripe 808 may include a third nutrient coating favorable for growing a third mold type. The fourth stripe 810 may include a fourth nutrient coating favorable for growing a fourth mold type. Within each stripe, different environmental conditions (e.g., temperature) may be applied during a measurement cycle by operation of the thermal control element. Within each stripe, different environmental sensors (e.g., temperature, humidity, pH) may be embedded on, in, or under the stripe to monitor the conditions that promote mold growth. The sensor information may be used to back-calculate the mold spore concentration in the air.

The segmentation of the test section 802 allows the mold sensor to efficiently detect the presence of different types of molds. Further, different stripe combinations may be produced depending on the types of mold expected to be present in the environment at a time of the test. Test sections having a single nutrient coating may not efficiently detect all types of mold. A further advantage of the stripes is that the mold sensor can provide a more detailed report on the types of mold that are present. By sensing the presence and/or concentration of mold in each of the stripes, a more detailed report can be provided.

Figure 9:
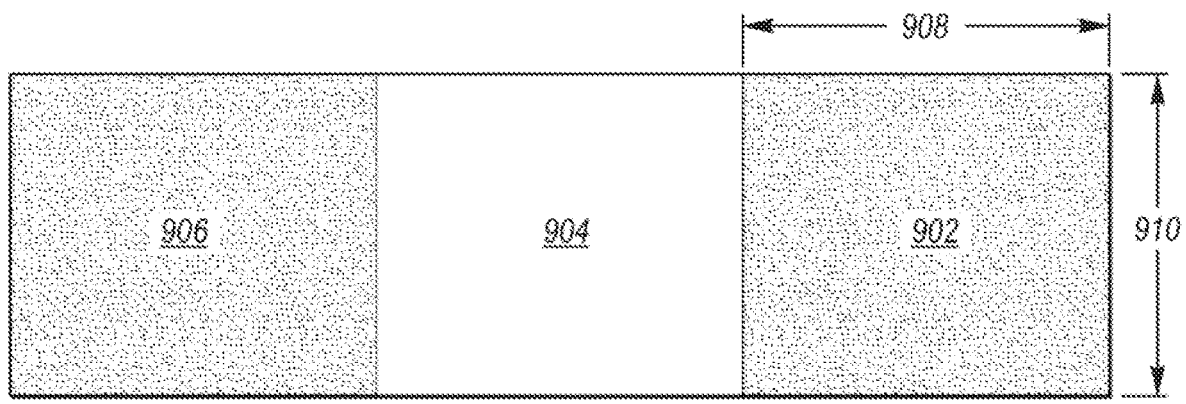
FIG. 9 depicts a growth surface having alternating sections of surface types.

FIG. 9 depicts another possible configuration for a growth medium 900. The growth medium 900 may be comprised of alternating growth areas defined on a substrate. The growth medium 900 may include a first growth area 902. Adjacent to the first growth area 902 may be a non-growth area 904. A second growth area 906 may be defined adjacent to the non-growth area 904. The pattern of growth areas and non-growth areas may be repeated for the entire length of the growth medium 900. The non-growth area 904 may be an area that is configured to avoid mold growth (e.g., not coated or having a coating with a high pH value). The non-growth area 904 may be an area that is not sticky or tacky. The non-growth area 904 may be configured to provide a buffer between the first growth area 902 and the second growth area 906. Each of the areas may be characterized by a width 910 and a length 908. The width 910 and length 908 may correspond to the dimensions of the chamber or dimensions of an opening for exposing the growth area 902 within the chamber. The dimensions of each alternating area may be similarly defined.

The alternating growth medium configuration 900 may be useful in configurations in which the area exposed to the air is outside of the chamber. In such configurations, continuous mold detection may not be desired. The non-growth area 904 may be positioned in the air-exposed region without concern that mold spores will adhere to the surface. When ready to perform a measurement cycle, the growth medium 900 may be advanced by the surface exchange mechanism to expose the second growth area 906 to air before advancing into the chamber. While the second growth area 906 is exposed to air, the non-growth area 904 may be within the chamber. Note that the first growth area 902 and the second growth area 906 may include stripes as described with reference to FIG. 8.

Figure 10:
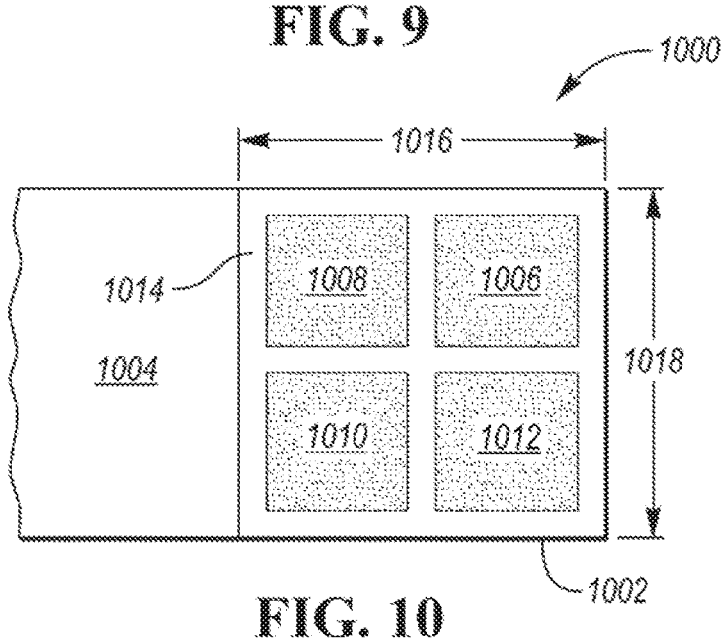
FIG. 10 depicts a growth surface including regions of different nutrient treatments.

FIG. 10 depicts an alternative configuration for a growth medium 1000. The growth medium 1000 may include a substrate material 1004. For example, the substrate material 1004 may be a film, membrane, or tape. The substrate material 1004 may be made of plastic, fabric or other material. In various configurations, the substrate material 1004 may be formed as a strip, a drum, or a disc. A plurality of test sections 1002 may be defined on the substrate material 1004. The test section 1002 may be defined as an area or surface of the growth medium 1000 that can be exposed within the chamber of the mold sensor. The test sections 1002 may be characterized by a width 1018 and a length 1016. The width 1018 and length 1016 may correspond to the dimensions of the chamber or dimensions of an opening for exposing the test section 1002 within the chamber. The test section 1002 may be repeated continuously on the substrate material 1004. During operation of the mold sensor, the test section 1002 may be exposed to air and processed through a measurement cycle. The remaining test sections defined on the substrate material 1004 may be enclosed by the surface exchange mechanism.

The test section 1002 may define one or more growth regions. For example, a first growth region 1006, a second growth region 1008, a third growth region 1010, and a fourth growth region 1012 may be defined. Each of the growth regions may have a coating or treatment that favors the growth of a different type of mold. For example, the first growth region 1006 may be treated with a first nutrient coating favorable for growing a first mold type. The second growth region 1008 may be treated with a second nutrient coating favorable for growing a second mold type. The third growth region 1010 may be treated with a third nutrient coating favorable for growing a third mold type. The fourth growth region 1012 may be treated with a fourth nutrient coating favorable for growing a fourth mold type. The test section 1002 may further include a non-growth area 1014. The non-growth area 1014 may be defined as the area within the test section 1002 that is between the growth regions. The non-growth area 1014 may be an area of the substrate material 1004 that is not treated to promote mold growth. The growth regions are depicted as squares but may be shaped differently. For example, the growth regions could be circular or rectangular. Further, while the pattern is shown as generally symmetric, the pattern could be non-symmetric. The test section 1002 may be repeated continuously on the substrate material 1004. During operation of the mold sensor, the test section 1002 may be exposed to air and processed through a measurement cycle. The remaining test sections defined on the substrate material 1004 may be enclosed by the surface exchange mechanism.

The test section 1002 may define a pattern that is repeated on the substrate material 1004. The pattern may repeat at a distance that is approximately the length 1016 of the test section 1002. Each of the growth regions may favor the growth of a specific type of mold. The division of the test section 1002 allows the sensor to efficiently detect the presence of different types of molds. Further, different growth region combinations may be produced depending on the types of mold expected to be present in the environment at a time of the test. A further advantage of the different growth regions is that the mold sensor can provide a more detailed report on the types of mold that are present. By sensing the presence and/or concentration of mold in each of the growth regions, a more detailed report can be provided. The non-growth area 1014 may be useful for sensor calibration. Since mold is not expected to grow on the non-growth area 1014, the mold sensor may utilize this area to calibrate the sensing device.

Features of each of the growth surface configurations may be combined to define additional growth surfaces. For example, the configurations of the FIG. 8 and FIG. 10 may include alternating regions that permit mold growth and prevent mold growth. The particular features selected for the growth surface may depend upon the mold sensor configuration. The growth surface configurations, while depicted as strips, may be formed on a surface of a drum or a disc in a corresponding manner.

The mold sensor configurations may include a surface exchange mechanism. In some configurations, the surface exchange mechanism may be configured as a single use cartridge that can be installed or removed from the mold sensor. The single-use surface exchange mechanism may include a fixed growth surface that is exposed in the chamber when the mechanism is attached to the mold sensor housing.

The surface exchange mechanism may also be configured to advance the growth surface in relation to the chamber. The surface exchange mechanism may be electrically controlled by the control device 116. The surface exchange mechanism may be configured to store a predefined amount of growth surface that may be fed into the chamber for a measurement cycle. The surface exchange mechanism may also be configured to stored used growth surface that has been processed through a measurement cycle.

Figure 11:
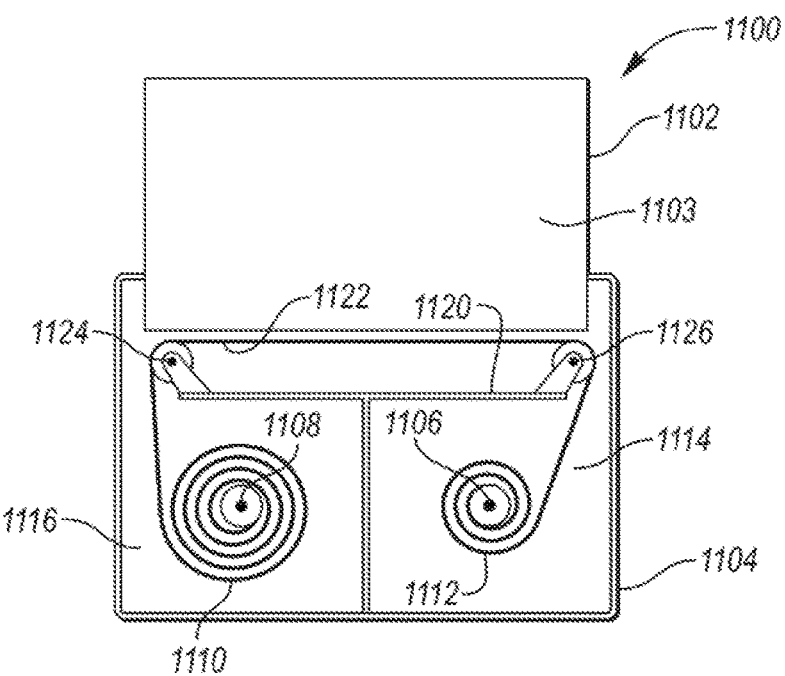
FIG. 11 depicts an example of a tape-based surface exchange mechanism.

FIG. 11 depicts a side view of a possible configuration of a tape-based surface exchange mechanism 1100 that is configured to advance a tape, membrane, or film. The tape-based surface exchange mechanism 1100 may include a tape housing 1104. The tape housing 1104 may define a used-tape chamber 1114 and an unused-tape chamber 1116. The housing 1104 may include a dividing wall 1118 between the used-tape chamber 1114 and the unused-tape chamber 1116. The tape housing 1104 may be configured to couple to a growth chamber housing 1102 that defines a growth chamber 1103.

The tape-based surface exchange mechanism 1100 may include a reel or spool 1108 that rotates about an axis. The tape-based surface exchange mechanism 1100 may include a driven reel or spool 1106 that is driven by an electrical drive unit. The electrical drive unit may be an electric motor having a shaft connected to an axis of the driven spool 1106. In some configurations, the electrical drive unit may include an electric motor coupled to the driven spool 1106 through one or more gears. In some configurations, a manual crank assembly may be attached to driven spool 1106 to permit manual advancement of the tape. The tape-based surface may be packaged such that the initial parameters (e.g., moisture level) of the tape are maintained until usage. For example, the exchange mechanism 1100 may include a liner or encapsulation that prevents moisture from evaporating from the tape-based surface before usage. The encapsulation may also prevent contamination of the tape-based surface before usage.

A length of unused tape 1110 or film may be wrapped around the spool 1108. The unused tape/film 1110 may be configured as a growth surface as previously described herein. The unused tape 1110 may be defined as that portion of the tape that has not been advanced to the growth chamber 1103. An end of the unused tape 1110 may be attached to the spool 1108. The tape may further include an active test surface 1122 that is defined as that portion of the tape that is positioned within the growth chamber 1103. The tape may further include a length of used tape 1112 or film that may be defined as that portion of the tape that has been processed through a measurement cycle in the growth chamber 1103. An end of the used tape 1112 may be attached to the driven spool 1106.

The tape housing 1104 may define a separating surface 1120 that is configured to separate the unused tape 1110 and used tape 1112 from the growth chamber 1103. The separating surface 1120 may define slots or openings through which tape may pass through. The tape-based surface exchange mechanism 1100 may further include a first guide roller 1124 that is configured to direct unused tape 1110 from the unused-tape chamber 1116 into the growth chamber 1103. The tape-based surface exchange mechanism 1100 may further include a second guide roller 1126 that is configured to direct tape (the active test surface 1122) into the used-tape chamber 1114. The first guide roller 1124 and the second guide roller 1126 may be coupled to the separating surface 1120 by a bracket. In some configurations, the bracket may include a compliant component that is configured to apply an amount of pressure to press the rollers against a bottom surface of the mold sensor housing 1102 to aid in sealing the chamber 1103 from outside air and/or to improve electrical contact between the tape and control device 116. A length of the first guide roller 1124 and the second guide roller 1126 may be defined by a width of the tape.

Unused tape (such as described by FIGS. 8-10) may be wrapped or spooled on the spool 1108. The tape may be routed via the first guide roller 1124 and the second guide roller 1126 so that an end may be attached to the driven spool 1106. The mold measurement cycle may be performed using the active test surface 1122 that is exposed within the growth chamber 1103. Upon completion of a measurement cycle, the driven spool 1108 may be rotated by the electrical drive mechanism. The driven spool 1108 may be driven to advance the portion of the tape that is the active test surface 1122 into the used-tape chamber 1114. By rotating the driven spool 1108 the tape will be advanced and wrap around the driven spool 1106. The rotation causes unused tape 1110 to unwind from the spool 1108 and advance into the growth chamber 1103 as the new active test surface 1122. The total length of the tape may be configured to perform a predetermined number of measurements.

In some configurations, the used-tape chamber 1114 may contain encapsulations and/or chemicals for inhibiting mold growth. This can prevent mold from growing in the unused-tape chamber 1116 and ensure that mold that was grown during the measurement is further destroyed. In some configurations, the unused-tape chamber 1116 may contain encapsulations and/or chemicals to maintain the unused tape 1110 for later use. For example, the encapsulations and/or chemicals may be configured to prevent the unused tape 1110 from becoming dry or non-sticky which could negatively impact the measurement effectiveness.

The tape-based surface exchange mechanism 1100 may be implemented as a cartridge that contains a predetermined length of tape or film. The cartridge may be user replaceable. The cartridge may be disposable after usage. In some configurations, the tape or film may be replaceable within the cartridge.

In some configurations, the tape or growth surface may include notches along one or both sides of the tape. For example, a notch may be placed to identify each test section of the tape. An optical sensor may be positioned to provide a signal when the notch appears between the source and receiver. The control device 116 may use the signal to properly position the tape so that a test section is properly exposed in the chamber. The sensor may also be used to measure the amount of tape that has been used. For example, the optical sensor may be used to count the notches. Knowing the distance between notches and/or a total number of notches on the tape, the control device 116 may compute the amount of tape used and/or the amount of tape remaining and communicate the values to the user. The control device 116 may compute the number of measurement cycles remaining based on the amount of tape remaining.

Figure 12A:
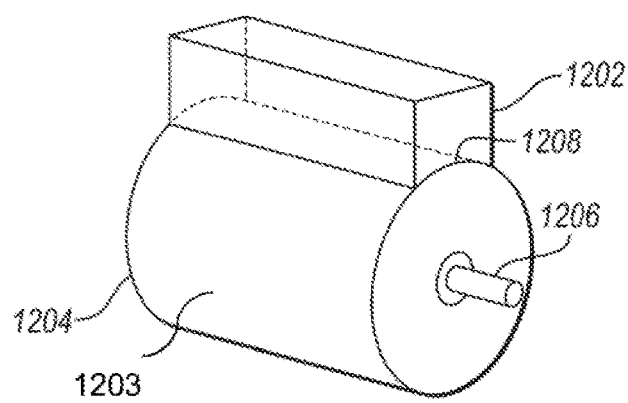
FIGS. 12A and 12B depict different views of a drum-based surface exchange mechanism.
Figure 12B:
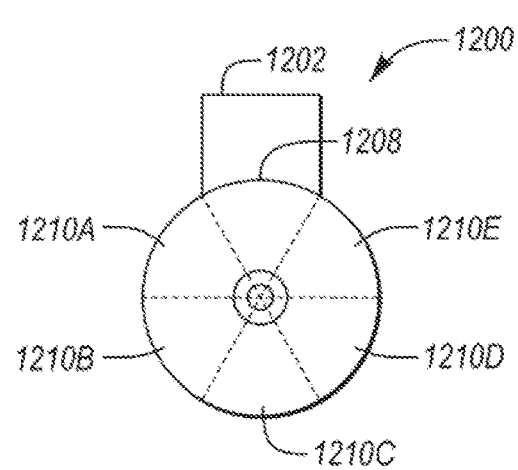

FIGS. 12A and 12B depict different views of a drum-based surface exchange mechanism 1200. The drum-based surface exchange mechanism 1200 may include a drum 1204. The drum 1204 may be cylindrically-shaped. In some configurations, the drum 1204 may be solid. In some configurations, the drum 1204 may be hollow with structural elements at each end to support and facilitate rotation of the drum 1204. The drum 1204 may be rotated by an electric motor 1206 having a shaft coupled to a central axis of the drum 1204. The drum 1204 may include a growth surface 1208 that may be defined as the area exposed within a growth chamber of a mold sensor housing 1202. The drum 1204 may include an unexposed surface 1203 that may be defined as the surface of the drum 1204 that is not exposed in the growth chamber of the mold sensor housing 1202. The drum-based surface exchange mechanism 1200 may include a housing (not shown) that is configured to attach to the mold sensor housing 1202 and support the electric motor 1206. The housing may further prevent exposure of the drum surface to external air.

The drum 1204 may be divided into a number of surface segments 1210. The surface segments 1210 may be configured to fit within the growth chamber of the mold sensor housing 1202. A number of surface segments 1210 may define the number of measurement cycles that may be performed. The surface segments 1210 may be striped or subdivided as previously described in relation to tape configurations.

The drum 1204 may be a replaceable element such that when all surface segments 1210 have been used, a new drum 1204 may be installed. The old drum may be discarded or recycled. In some configurations, the drum surface may be a replaceable sheet or substrate. The used drum surface sheet may be replaced by a new drum surface sheet.

The drum-based surface exchange mechanism 1200 may rotate by operation of the electric motor 1206. A measurement may be performed using the growth surface 1208 that is exposed in the chamber of the mold sensor housing 1202. After the measurement cycle is completed, the electric motor 1206 may be actuated to advance the drum 1204 to place a next surface segment 1210 into the growth chamber defined by the sensor housing 1202. For example, in FIG. 12B, the current segment exposed in the mold sensor housing 1202 is the growth surface 1208. Assuming a clockwise rotation, the surface segment 1210A may advance into the mold sensor housing 1202. The control device 116 may be configured to actuate the electric motor 1206 for a predetermined duration calibrated to rotate the drum 1204 an amount corresponding to one of the surface segments 1210. In other configurations, a sensor, such as a potentiometer or encoder, may be used as a feedback signal to measure the amount of rotation and drive the electric motor 1206 accordingly. In some configurations, a manual crank assembly may be attached to axis of the drum 1204 to permit manual advancement of the drum 1204.

Figure 13A:
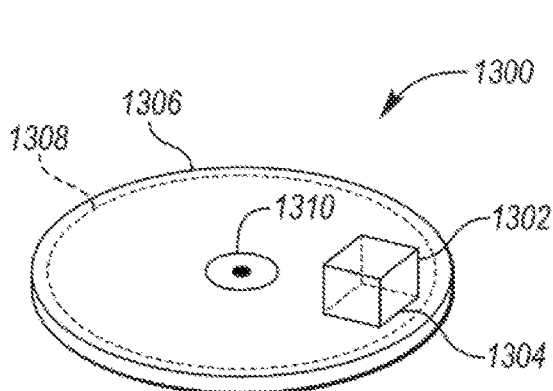
FIG. 13A depicts an example of a disc-based surface exchange mechanism.

FIG. 13A depicts a disc-based surface exchange mechanism 1300 for advancing a disc 1308 to position a growth surface 1304 within a chamber formed by the sensor housing 1302. The disc-based surface exchange mechanism 1300 may include a disc housing 1306 that is configured to enclose the disc 1308. The disc 1308 may be configured to rotate about a central axis. An electric motor 1310 may be coupled to the disc housing 1306. A shall of the electric motor 1310 may be coupled to the disc 1308 to facilitate rotating the disc 1308.

Figure 13B:
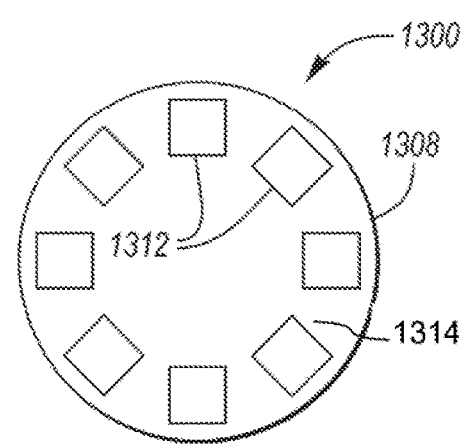
FIG. 13B depicts an example of disc configuration for the disc-based surface exchange mechanism.

In some configurations, the entire surface of the disc 1308 may be treated to promote mold growth. The disc 1308 may also be configured as depicted in FIG. 13B. The disc 1308 may define growth areas 1312 that are treated to promote mold growth as previously described herein. The disc 1308 may include a non-growth area 1314 that separates the growth areas 1312. The non-growth area 1314 may prevent mold growth from spreading outside of the sensor housing 1302. The growth areas 1312 may be divided into differently treated regions to promote growth of different types of mold as described previously herein.

The disc-based surface exchange mechanism 1300 may position the disc 1308 by operation of the electric motor 1310. A measurement may be performed using the growth surface 1304 that is exposed in the growth housing 1302. After the measurement cycle is completed, the electric motor 1310 may be actuated to rotate the disc 1308 to the next growth area 1312. The control device 116 may be configured to actuate the electric motor 1310 for a predetermined duration calibrated to rotate the disc 1308 an amount corresponding to one of the growth areas 1312. In other configurations, a sensor, such as a potentiometer or encoder, may be used as a feedback signal to measure the amount of rotation and drive the electric motor 1310 accordingly.

The mold sensor configurations include a sensing device configured to detect mold. The sensor may be electrically coupled to the control device 116. A variety of sensor technologies are adaptable to detecting mold growth within the housing. The types of sensors that may be used include optical sensors, chemical sensors, biosensors, mechanical sensors, audio sensors, and electrical sensors. The sensors may be configured to measure visual, mechanical, electrical, biological, and/or chemical properties associated with mold growth. The mold sensor configurations may include different types of sensors to detect the presence of mold. Some sensor technologies may be better suited for detecting the concentration of mold, while others may be suited for detecting the presence of mold growth.

Referring to FIG. 1 as an example, the sensing device 110 may be implemented in a variety of ways. Various configurations may rely on different sensor technologies. The types of sensing device may be a chemical/gas sensor, an electrical sensor, a biological sensor, an optical sensor, a mechanical sensor, or an audio sensor. The type of sensing device may depend on the type of properties associated with the presence and/or concentration of mold that are to be detected. The sensing device 110 may be configured to detect mold by measuring optical properties, electrical properties, biological properties, mechanical properties, and/or chemical properties. The different properties may be detected by different types of sensors. For example, some chemical properties, such as pH, may be detected by optical and/or electrical sensors. Mechanical properties may be detected by electrical and/or optical sensors. The sensing device may be characterized by the physical property that it is attempting to measure and how it measures the physical property.

Mold spores release microbial volatile organic compounds (mVOCs) as a byproduct during its metabolism. Mold spores may further release mycotoxins during a second metabolism as an end product. Mold growth may be detected by sensing these chemicals during the mold lifecycle. The sensing device 110 may be a chemical sensor that is configured to sense the changes in mVOCs or other chemicals associated with mold growth.

Mold may release alcohol, aldehyde, hydrocarbons, acids, ether, esters, ketones, terpenoids, sulfur, nitrogen and other compounds. The type of chemicals released may depend upon the type of mold that is growing. The sensing device 110 may be any type of chemical sensor that can detect these compounds. For example, the sensing device 110 may be an electrochemical gas sensor or a metal oxide gas sensor that is configured to detect these compounds. In some configurations, the sensing device 110 may include a plurality of chemical sensors that are each configured to measure a specific chemical compound.

For example, the sensing device 110 may be a solid-state chemiresistor sensor that changes resistance in response to exposure to certain chemical compounds. The control device 116 may be programmed to estimate a gas concentration by measuring the resistance of the chemiresistor sensor. The control device 116 may include a voltage divider network and an analog-to-digital (A2D) converter to measure a voltage across the chemiresistor sensor. The control device 116 may store a table or tables that map voltage and/or resistance values to gas concentrations. The control device 116 may be configured to generate a warning or alarm responsive to the gas sensor signal being indicative of mold concentrations exceeding a threshold. For example, the warning may be generated when the mold concentration exceeds a reference concentration by more than a predetermined amount.

The control device 116 may store data that relates the chemical sensor measurements to mold growth. The data may be experimentally derived from testing. The stored data may indicate gas types and levels during different phases of mold growth. In addition, the stored data may include a gas profile for different types of mold. The control device 116 may sample the chemical/gas sensor over time and compare the results to the stored data to further identify a type of mold, concentration of mold, or growth phase of the mold. In addition, the initial concentration of mold before mold growth may be determined by back-calculating and estimating the amount of growth based on data that may be experimentally derived from testing.

Mold growth may also change the properties of the growth medium as the mold grows. Common mold types such as *Aspergillus* and *Penicillium* families shift the pH of the growth surface 112 towards acidity. The sensing device 110 may be configured to sense a change in pH caused by mold growth. A first technique for detecting the pH of the growth surface 112 includes adding a universal pH indicator solution to the growth surface 112. The universal pH indicator may change in color as the pH of the growth surface 112 changes. The nutrient treatment for the growth surface 112 may include the universal pH indicator solution. The sensing device 110 may be configured to detect color changes of the growth surface 112 that are associated with the pH changes. In some configurations, the sensing device 110 may be a camera that provides a color image of the growth surface 112. For example, the camera may be a charge-coupled device (CCD) configured to provide a digital image of the growth surface 112. The control device 116 may be configured to implement image processing algorithms to determine changes in color of the growth surface 112. The sensing device 110 may be an optical sensing device that is configured to output an electromagnetic wave (e.g., light) and receive a reflected wave from the growth surface 112.

The color change caused by pH changes may be detected by changes in the optical properties such as adsorption, reflection, scattering, color, and/or fluorescence. The properties may be detected with an optical sensing system, an imaging system, or a camera system. For example, the optical sensing system may be configured to provide data regarding color of the mold growing on the surface. The control device 116 may be programmed to process the optical data including color information to identify a color of the mold growth or substrate. The color information may be indicative of mold growing on the substrate. For example, a change in pH of the substrate may be identified by a change from a baseline color to a predetermined color. The predetermined colors indicative of mold growth may be derived from experiments.

As shown for example in FIG. 2, the sensing system may incorporate a sensor source module 210 and the sensor receiving module 212. While FIG. 2 depicts the sensor receiving module 212 being on the opposite side of the growth surface 112 relative to the sensor source module 210, the sensor receiving module 212 may be placed on the same side of the growth surface 112 as the sensor source module 210.

The sensor source module 210 may be a light source (or electromagnetic wave source) and the sensor receiving module 212 may be a photodetector. For example, the photodetector may be placed below the growth surface 112. The light source may be activated to produce an electromagnetic wave in the chamber 103 to illuminate/irradiate the growth surface 112. Electromagnetic waves passing through the growth surface 112 may change wavelength based on the color of the growth surface 112. The photodetector (sensor receiving module 212) may receive the electromagnetic waves and generate an electrical signal. The photodetector may be configured to detect different wavelengths of electromagnetic waves so that different colors may be detected. In some configurations, multiple photodetectors (e.g., photodetector array) may be implemented with each photodetector tuned for a given wavelength range.

The optical sensing systems, imaging systems or camera systems may include both the sensor source module 210 (e.g., optical source, LED, laser) and the sensor receiving module 212 (e.g., optical sensor, photodiode, photodetector, imager, camera). In some configurations, the optical source may be a source illuminating divergent beam configured to illuminate a large area or entire area of the growth surface 112 within the chamber 103. The optical source may be a light source combined with beam divergence component that diverges the beam to illuminate a large area or entire area of the growth surface 112 within the chamber 103. The optical sensor may be an array of photodiodes or a camera that is configured to receive electromagnetic waves reflected or scattered from and/or transmitted through the growth surface 112. In this configuration, the optical property changes of the entire growth surface 112 can be collected at the same time. The sensor source module 210 may be driven by one or more input signals generated by the control device 116. The sensor receiving module 212 may provide optical data that is indicative of one or more optical properties to the control device 116. The optical data may be provided as one or more electrical signals. In some examples, the optical data may include digital data such as image or pixel data/patterns. The specific optical data provided by the sensor receiving module 212 may depend on the type of sensor being utilized.

In another configuration, the optical source may be a laser beam with high directivity and small divergence angle, and the optical sensor may be either a single photodiode or an array of photodiodes or optical sensors. The optical source may be driven by a driver or electric motor to sweep around the entire or large proportion of the growth surface 112, and the single photodiode may also be driven by the same or separate driver or electric motor to move with the source accordingly. This configuration may be useful for configurations in which different regions of mold growth are defined. Each region may be scanned for the presence of mold. The region in which mold is detected may be stored and may indicate the type of mold that is present. The array of photodiodes or optical sensors may or may not need to move.

The optical source can be either single wavelength source or a source that outputs multiple wavelengths (e.g., broad bandwidth source), and the optical sensor may be either a narrow bandwidth or a broad bandwidth sensor accordingly. Optical property changes of the growth surface 112 may be detected in the ultraviolet (UV) wavelength range, the visible wavelength range or the infrared (IR) wavelength range depending on the specific growth surface 112 and mycelium that is growing in the chamber 103. If the optical source is a multi-wavelength or broadband source, an optical spectrometer may also be used as the optical sensor to detect the optical property changes in a spectra range. The spectra information may also contain mVOC or other information and both growth surface 112 optical property changes and mVOC or other information change may be detected in this way.

The optical source can also be an array of individual monochromatic optical lasers. For example, ultraviolet lasers can induce fluorescence when illuminating the mold spores. With two or more ultraviolet lasers configured as the optical source and an optical spectrometer as the optical sensor, the fluorescence of mold spores can be detected. Mold spores may be detected by signatures of fluorescence spectra.

The absorption, reflection and/or scattering change induced by mold growth may be detected directly by the light intensity received by the photodetector. The color change induced by mold growth may be determined using a filter with a photodiode (or array), and RGB pixel (or RGB pixel array). The control device 116 may incorporate algorithms to detect changes in intensity and/or color.

In addition to growth in the plane of the growth surface 112, the mold may grow out of the plane. A vertical depth of the mold may increase as the growth time increases. The optical sensor may be configured as a laser-ranger finder (e.g., based on time-of-flight, frequency modulated continuous wave, or structured-light technology) to detect the out-of-plane depth of the growing mold. The control device 116 may be configured to periodically measure the range finder to monitor the vertical growth of the mold. The control device 116 may compute a rate of change of the vertical growth.

The optical properties of the growth surface may be calibrated with a reference before exposure to mold or mold growth and saved for comparison with the optical properties observed after exposure and growth. The mold growth affects the optical properties within the chamber. By comparing the measurement results with baseline results, the control device 116 may determine the presence of mold and the initial concentration of mold.

Another technique for detecting the pH of the growth medium may be to utilize a pH meter such as a potentiometric pH meter. The growth medium may include pre-printed electrodes for the potentiometric sensor. The surface above the electrodes may be coated with nutrients to promote mold growth. As the pH changes, the resistance measured between the electrodes may change. The pH level may be determined by measuring the resistance between the electrodes. The control device 116 may be configured to receive the electrical signal and estimate the resistance. Electrical sensing is described in additional detail herein.

Figure 19:
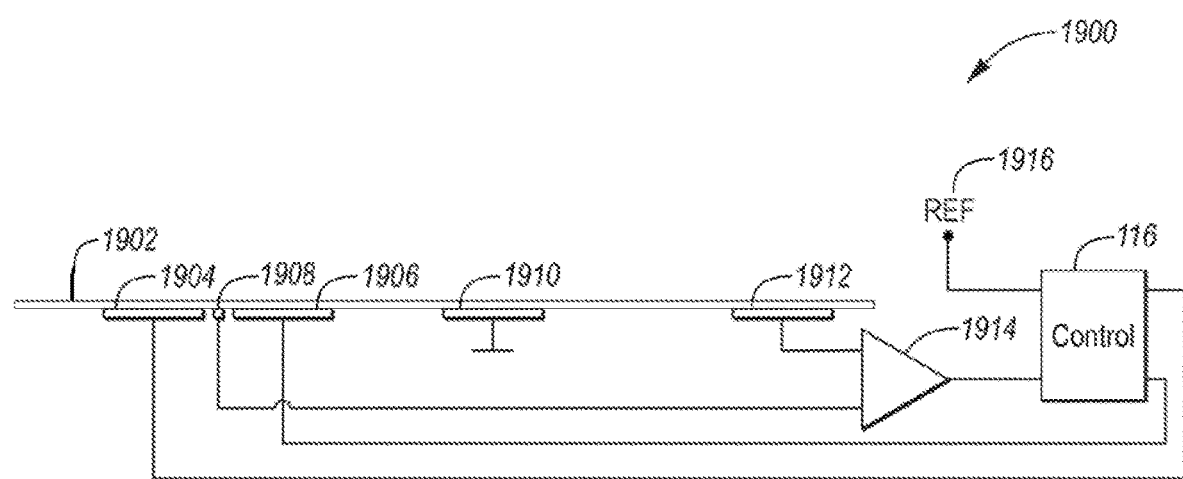
FIG. 19 depicts an example of a growth surface configured to measure and control a pH level of the growth surface.

Another technique for detecting the pH may be to implement a system that controls the pH of a small region of the growth medium. FIG. 19 depicts a configuration for controlling the pH of a surface. An active area of the growth surface 1902 may be covered by a hydro gel or similar coating that permits diffusion and promotes mold growth. The pH sensor may include a sense electrode 1908 that is integrated with the growth surface 1902. The sense electrode 1908 may have a proportional electrical potential response to pH with respect to a reference electrode 1912. A current source may supply current to one or more working electrodes (e.g., first working electrode 1904 and second working electrode 1906) which then flows through one or more counter electrodes 1910. The control device 116 may control the current to maintain the sensing electrode 1908 at a reference pH level 1916 that may be a constant pH value. This may be used to create a predetermined pH environment to promote the growth of certain types of mold. This also provides a feedback signal to provide a measure of the amount of feedback that must be applied to maintain the pH at a constant level. An amplifier 1914 may receive inputs from the sense electrode 1908 and the reference electrode 1912. The output of the amplifier 1914 may be electrically coupled to the control device 116. As the pH level of the growth surface 1902 changes due to mold growth, the amount of current supplied to the working electrodes 1904, 1906 may change. As a result, the voltage measured at the sense electrodes 1908 changes.

The configuration of FIG. 19 may be applied to create a certain pH environment that promotes growth of certain types of mold. The feedback signal from the sense electrode 1908 is proportional to an amount of current that must be applied to keep the pH constant. For example, if no mold is growing, the pH level should remain constant without changes to the current. As mold grows on the surface, the pH level changes causing the control device 116 to apply more current to rebalance the pH level. Mold growth may be detected by monitoring the feedback signal for changes. If the feedback signal exceeds a predetermined threshold, mold may be present. The growth surface may be configured with multiple areas configured as shown in FIG. 19. Each of the areas may be used to create a different pH environment for mold growth. In addition, different areas may be configured to be in a different temperature zone (e.g., by operating thermal control elements associated with each of the areas). In this manner, the environment may be configured to efficiently grow different types of mold.

Mold growing on the growth surface 112 may change electrical properties of the surface. For example, impedance, capacitance, frequency response, and/or other electrical properties of the growth surface 112 may be altered due to mold growth. Properties of the growth surface 112 can change due to mold growth as the mold feeds on the nutrients in the growth surface 112 and its roots (mycelium) spread to reach more nutrients. The changes in both the growth surface 112 and the intrusion of the mycelium cause changes in impedance, capacitance, frequency response, and other electrical properties.

Figure 14:
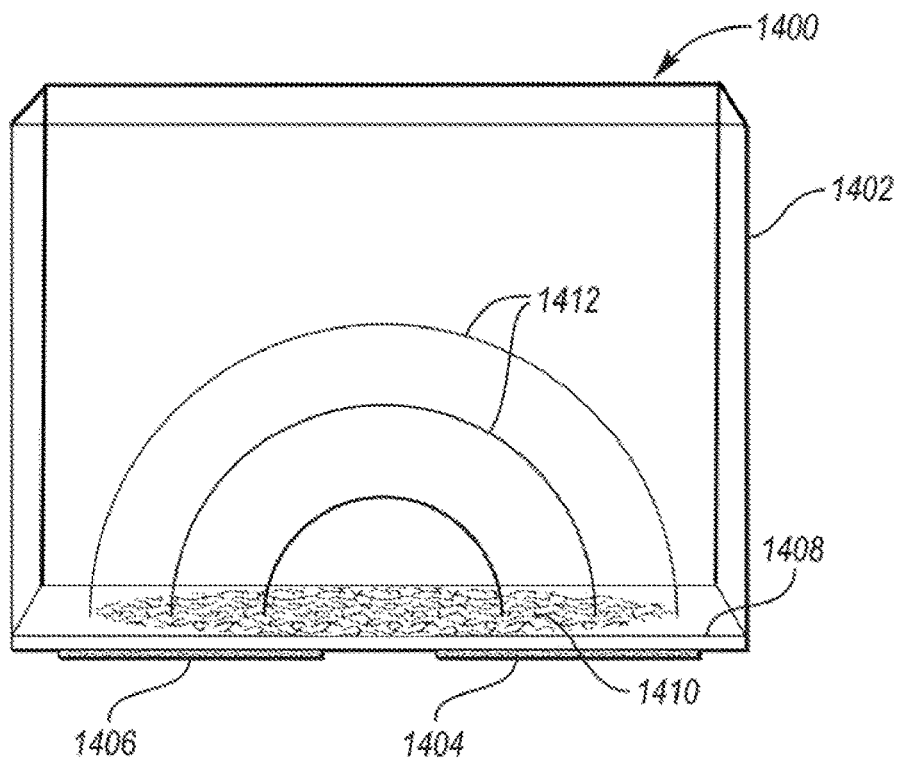
FIG. 14 depicts a possible configuration for a capacitive-type sensor for detecting mold on a growth surface.

FIG. 14 depicts a sensing device configured to measure the electrical properties. The electrical sensing configuration 1400 may include a first electrical contact 1404 and a second electrical contact 1406 that are coupled to a growth surface 1408. The first electrical contact 1404 and the second electrical contact 1406 may be adhered or deposited on the growth surface 1408. In some configurations, a substrate of the growth surface 1408 may be a film and the contacts may be deposited or etched onto the substrate.

A voltage may be applied across the first electrical contact 1404 and the second electrical contact 1406. The voltage may create electric fields 1412 within the housing 1402 and the growth surface 1408. The first electrical contact 1404 and the second electrical contact 1406 may operate as a capacitance sensor. A dielectric between the first electrical contact 1404 and the second electrical contact 1406 may be defined by the growth surface 1408, mold 1410, and air with the housing 1402. As the mold 1410 grows on the growth surface 1408 and into the chamber defined by the housing 1402, the dielectric properties may change. By measuring the dielectric change over time, the system may detect mold growth, concentration of mold, and/or types of mold. The first electrical contact 1404 and the second electrical contact 1406 may be electrically coupled to the control device 116. The control device 116 may be configured to supply a voltage across the first electrical contact 1404 and the second electrical contact 1406. The sensing device may include a current sensor to measure current flowing between the first electrical contact 1404 and the second electrical contact 1406. The control device 116 may be configured to generate an alternating current (AC) voltage waveform with a range of frequencies and magnitudes. By applying a known voltage waveform and measuring the resulting current, the control device 116 may determine the capacitance using basic electrical relationships. As the mold 1410 grows and changes the dielectric, the capacitance value may change. The control device 116 may be configured to sweep the frequency to obtain a frequency response of the dielectric properties.

Figure 15:
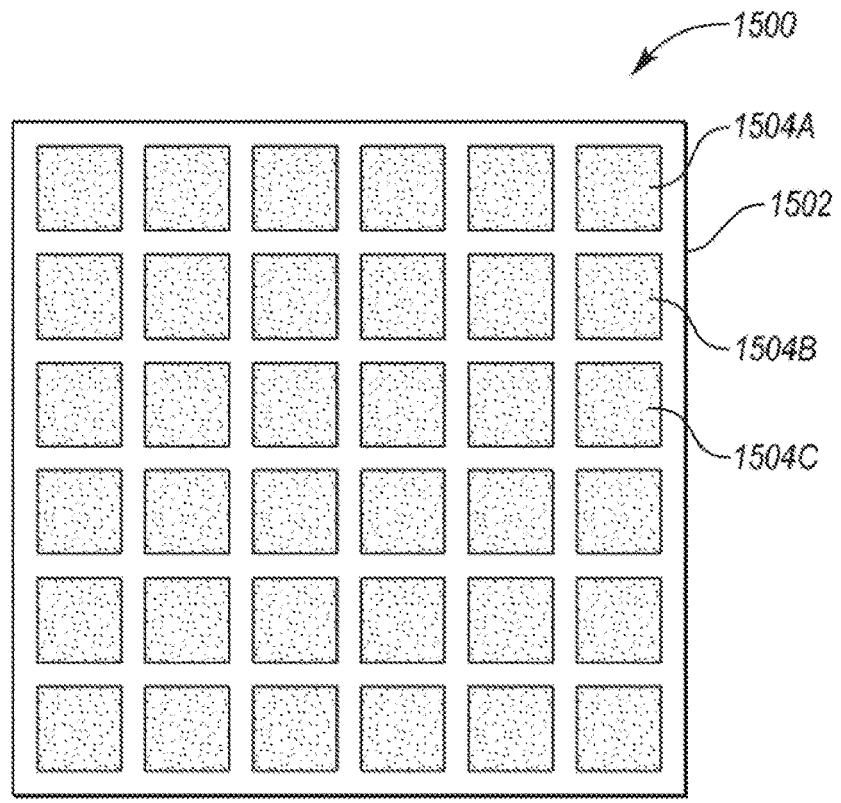
FIG. 15 depicts a possible configuration for growth surface with integrated electrical contacts.

FIG. 15 depicts a capacitive sensor 1500 that includes a plurality of electrical contacts 1504 that are coupled to or integrated with a growth surface 1502. The electrical contacts 1504 may be arranged as a grid or other pattern. Each of the electrical contacts 1504 may be electrically coupled to the control device 116 (e.g., by a matching grid of electrodes). The control device 116 may be configured to measure the capacitance across any pair of electrical contacts 1504 as described previously herein. The arrangement of the capacitive sensor 1500 allows for mold growth to be detected on different areas of the growth surface 1502. By dividing the growth surface 1502 into smaller regions, mold growth may be determined in less time. The capacitive sensor 1500 can also identify the specific region on the growth surface 1502 at which mold is growing. This may be particularly useful when the growth surface 1502 is configured with different nutrient treatments in different regions (e.g., FIG. 8 and FIG. 10). The control device 116 may be configured to apply a voltage between any pair of contacts 1504 and measure a corresponding current. The control device 116 may identify mold growth between the pair of contacts when the capacitance changes by a predetermined amount.

Figure 16:
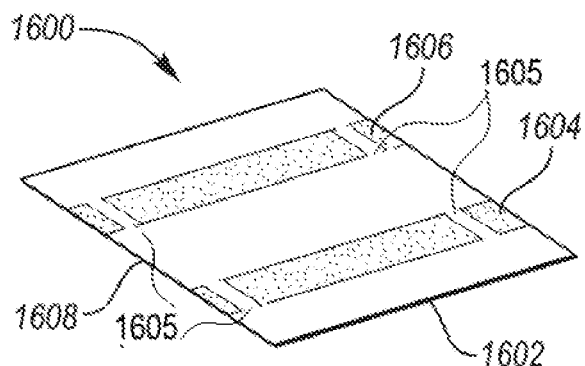
FIG. 16 depicts an example of a growth surface with conductive strips.

FIG. 16 depicts a possible configuration for an electrical sensing growth medium 1600 for detecting electrical properties of a growth surface 1602. The growth surface 1602 may include conductive strips that can be electrically excited to measure the electrical properties. A first conductive strip 1604 and a second conductive strip 1606 may be attached to the growth surface 1602. Between the first conductive strip 1604 and the second conductive strip 1606 may be a mold growth area 1608. The mold growth area 1608 may be treated with nutrients to encourage mold growth. Mold growing in the growth area 1608 may change the electrical properties between the conductive strips. The conductive strips may also be configured to be perpendicular to the depiction in FIG. 16. Other configurations of the conductive strips are possible (e.g., circular, arcs). The first conductive strip 1604 and the second conductive strip 1606 may include periodic gaps 1605 or openings so that a measurement is only affected by the growth surface 1602 that is within the growth chamber.

Figure 17:
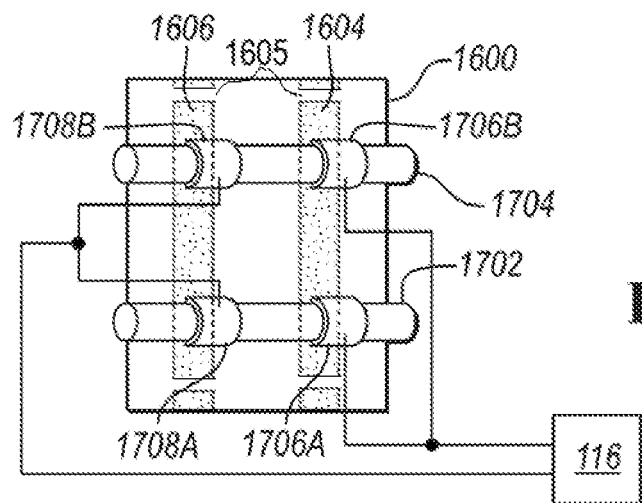
FIG. 17 depicts an example of a roller-based electrical contact for interacting with conductive strips of a growth surface.

FIG. 17 depicts a first electrical sensing configuration in which electrical contact with the conductive strips is via rollers of the surface exchange mechanism. The electrical sensing configurations may utilize a sensing device that is installed on a bottom-side of the growth surface 1602. The surface exchange mechanism may include a first roller 1702 and a second roller 1704 that are in contact with the electrical sensing growth medium 1600 while the growth surface 1602 is within the chamber 103. One or more of the first roller 1702 and the second roller 1704 may include conductive contacts about the circumference of the corresponding roller. The conductive contacts may extend around the rollers so that the conductive contacts may contact the electrical sensing growth medium 1600 at any rotational position of the rollers. For example, the first roller 1702 may include a high-side contact 1706A that is electrically coupled to the control device 116. The first roller 1702 may include a low-side contact 1708A that is electrically coupled to the control device 116. The second roller 1704 may include a high-side contact 1706B that is electrically coupled to the control device 116. The second roller 1704 may include a low-side contact 1708B that is electrically coupled to the control device 116. The high-side contacts 1706 on the rollers may be configured to align with the first conductive strip 1604 of the electrical sensing growth medium 1600. The low-side contacts 1708 of the rollers may be configured to align with the second conductive strip 1606 of the electrical sensing growth medium 1600. Electrical connection of the contacts 1706, 1708 to the control device 116 may be through a slip ring or similar device.

As the growth surface 1602 of the electrical sensing growth medium 1600 is advanced, the conductive strips may maintain contact with the contacts of the rollers. The gaps 1605 may limit the measurement to that surface that is within the chamber. In this manner, the regions of the tape outside of the chamber do not affect the measurement. The control device 116 may measure the electrical properties of the electrical sensing growth medium 1600 by exciting the conductive strips. For example, the control device 116 may be programmed to apply a voltage or potential across the high-side contact 1706 and the low-side contact 1708. The voltage may cause a current to flow that is proportional to the impedance of the mold growth area 1608. The control device 116 may measure the current that flows and can determine the resistance by application of Ohm's law. The control device 116 may supply an AC voltage and sweep the frequency through a predetermined range to further characterize the impedance and/or frequency response of the growth area 1608.

For configurations having the conductive strips perpendicular to those depicted, the rollers may be constructed of a conductive material and be electrically connected to the control device 116. The conductive strips of the electrical sensing growth medium may be spaced at a distance corresponding the distance between the rollers. In this configuration, one roller may contact a high-side conductive strip and the other roller may contact the low-side conductive strip. The conductive strips may further include gaps and the conductive surface of the rollers may include corresponding gaps.

Figure 18A:
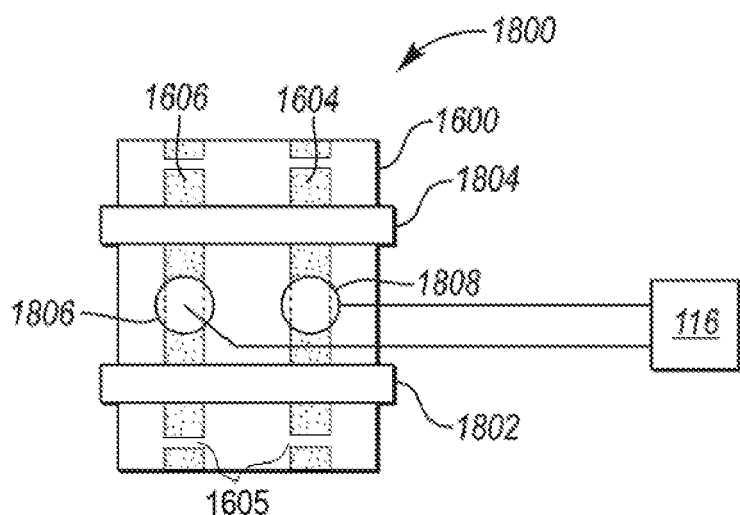
FIGS. 18A and 18B depicts different views of an electrode-based electrical contact for interacting with conductive strips of a growth surface.

FIG. 18A depicts a second electrical sensing configuration 1800 that relies on electrodes to interface with the conductive strips in the electrical sensing growth medium 1600. The second electrical sensing configuration 1800 may include a first electrode 1806 and a second electrode 1808. The first electrode 1806 and the second electrode 1808 may be constructed of a conductive material and may be electrically connected to the control device 116. The first electrode 1806 may align with the second conductive strip 1606 of the electrical sensing growth medium 1600. The second electrode 1808 may align with the first conductive strip 1604 of the electrical sensing growth medium 1600. The electrical sensing growth medium 1600 may contact a first roller 1802 and a second roller 1804 that are associated with the surface exchange mechanism.

Figure 18B:
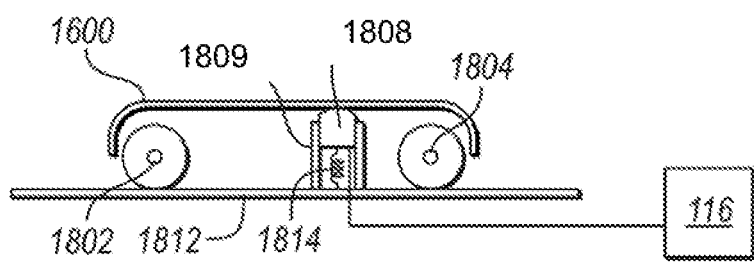

FIG. 18B depicts a side view of the second electrical sensing configuration 1800 that provides more detail with respect to the second electrode 1808. The second electrode 1808 may be fit within an electrode housing 1809. The electrode housing 1809 may be sized to partially contain the second electrode 1808 and allow movement of the second electrode 1808 toward and away from the electrical sensing growth medium 1600. A spring mechanism 1810 (or other compliant element) may be positioned in the electrode housing 1809 and under the second electrode 1808. The spring mechanism 1810 functions to provide a force to the second electrode 1808 to maintain contact with the surface of the electrical sensing growth medium 1600. The electrode housing 1809 may be coupled to a mounting surface 1812 that may be part of the surface exchange mechanism structure. Other electrodes may be similarly configured. The first roller 1802 and the second roller 1804 may contact the electrical sensing growth medium 1600 to facilitate movement. The first roller 1802 and the second roller 1804 may also apply sufficient pressure to the electrical sensing tape 1600 to ensure that the chamber is sealed. The first roller 1802 and the second roller 1804 may be coupled to the mounting surface 1812 via brackets.

The control device 116 may be configured to measure a baseline impedance characteristic before mold grows on the growth surface. The control device 116 may then monitor for changes in the impedance characteristics that are indicative of mold growth. The control device 116 may store data related to impedance characteristics for different types and concentrations of mold. The control device 116 may compare measured impedance characteristics to the stored characteristics to identify a type of mold and/or concentration of mold within the chamber.

The electrical sensing configurations may further include features to enhance electrical contact between the conductive strips of the growth surface and the sensing elements. For example, the electrical sensing configurations may include one or more magnets or electromagnetics arranged to magnetically attract the growth surface. For example, the conductive strips may be comprised of nickel. An electromagnet may be positioned beneath the conductive strips near the electrode or roller (e.g., near where the electrical contact takes place) and energized when electrical contact is desired. The electromagnet may attract the conductive strip and ensure contact with the electrode or roller contact. The feature is useful when the growth surface can be moved as electrical contact may be broken during the moving process. The mechanism for reestablishing an electric connection between the growth surface and sensing device ensures reliable performance.

In some configurations, mold may be detected using biological or chemical elements as a binding or reaction agent for sensing purposes. The biological or chemical elements may be configured to bind or react with mold spores. For example, certain antibodies or enzymes bind with certain types of mold and binding events may be detected using various sensing methods (e.g., change in electrical properties). Further, the reaction between the mold spores and the biological or chemical elements may cause the release of chemical compounds. The released compounds may be detected with sensors such as chemical, optical, and electrical sensors. The binding or reaction event may be used to determine the presence of different mold types. The binding or reaction agent may also be used to capture mold spores before the growth stage. Different biological or chemical elements may also be used to either promote or retard mold growth.

In some configurations, mold may be detected using an audio-based sensing device. The growing mold may influence the manner that sound travels within the chamber. Due to the mechanical nature of the molecular structure, growing mold will absorb and reflect sound waves of certain frequencies. In some configurations, the sensing device may include a source configured to emit a sound wave and a receiver configured to convert the sound signals to electrical signals. The configuration may depend on the type of sound to be measured. In a configuration that measures the reflection of the sound waves, a source module 210 and a receiving module 212 may be installed within the chamber (e.g., same side of growth surface). The receiving module 212 receives sound waves that are reflected from the growth surface 112. In some configurations, the sensing device may be an ultrasound transceiver that includes the source module and receiving module. In a configuration that measures the transmission of the sound waves through the growth surface 112, the source module 210 and the receiving module 212 may be mounted on opposite sides of the growth surface 112 (e.g., depicted in FIG. 2). For example, the sensor source module 210 may be an ultrasound speaker and the sensor receiving module 212 may be a microphone configured to convert sound signals to an electrical signal. The sensor source module 210 may be driven by the control device 116. The control device 116 may operate the sensor source module 210 to output a frequency sweep in a predetermined range of frequencies. The control device 116 may receive the electrical signals from the sensor receiving module 212 and may measure the magnitude of the received sound signal. The control device 116 may be configured to estimate the molecular resonance frequency of the mold to determine the specific type of mold that is growing.

The control device 116 may store previously generated sound profiles that represent different mold types and concentration levels. The control device 116 may be configured to compare a measured sound profile to the stored sound profiles to identify a type and/or concentration level of the mold that is growing in the chamber 103. In some configurations, the control device 116 may recognize mold growth by a change in the sound profile as compared to a baseline sound profile. Additional sensors may be incorporated (e.g., to measure volume or weight) to provide an improved estimation.

An ultrasound sensor may also be used to sense the out-of-plane growth of the mold by outputting a sound pulse and measuring the response time (e.g., time for sound to travel to the receiver). A larger vertical growth may result in a shorter return time of the pulse. The sensing device may include an ultrasound emitter and an ultrasound receiver to measure the response time. The control device 116 may include circuitry to generate the ultrasound signal and receive the reflected ultrasound signal. The control device 116 may include circuitry and/or control logic to sense the delay between sending the ultrasound signal and receiving the reflected signal. The control device 116 may be programmed to measure the height of the out-of-plane mold growth. The height may be monitored over time and stored. The control device 116 may store data regarding mold growth patterns for different types of molds. For example, mold growth patterns may be experimentally derived by testing. The mold type may be determined by comparing the measured growth pattern to the historical patterns.

In configurations utilizing an audio-based sensing device, the enclosed volume or chamber may be sound/audio isolated from the outside. For example, the chamber may be coated with a material to minimize sound echo. In addition, this prevent outside noise/sounds from disturbing the measurement process within the chamber 103. The housing 102 may also be configured to optimize the audio/sound properties within the chamber 103 to minimize unwanted echoes or reflections. An additional microphone may be attached outside of the chamber 103 and be used to subtract external noises from the measurement signal to improve the accuracy of the measurement (e.g., differential measurement).

The growth surface may also have certain mechanical properties (e.g., inertia, mass). The surface may vibrate or oscillate when excited by a sound wave. The vibration may be characterized by an amount of damping. The damping may be characterized as how quickly the magnitude of the vibration or oscillation dissipates after the excitation stops. A thicker layer of mold growth may result in more damping of the growth surface. That is, the vibrations of the growth surface will dissipate is less time. The audio sensor source may be used to excite the growth surface using sound waves to cause vibrations that may result in changes in the response times from the emitter to the receiver. A first baseline may be established prior to exposing the growth surface to external air and a second baseline may be established prior to growing mold. For example, the audio signal may cause a vibration or deflections in the growth surface that may be measured. After exposure and mold growth, the measurements may be repeated and compared to the second baseline. An increase in damping may be indicative of mold growth on the surface. The magnitude of the increase in damping may be indicative of the amount of mold growth that has occurred. Multiple ultrasound speakers may be employed to create a stereo effect for measurements.

Experimental testing may be performed to determine the damping properties of mold growth in the chamber. Under controlled conditions, mold may be grown, and the damping properties may be measured at different growth stages. The data may be stored for different types of mold. The control device 116 may store the data for later comparison. By comparing a damping response to historical damping responses, the control device 116 may be able to determine the stage of growth, concentration, and/or the type of mold that is growing.

Mold may be detected by measuring mechanical properties of the growth surface that are changed by mold growth. The mechanical properties may be measured by applying actuation pulses and measuring the resulting frequency and/or amplitude responses. In some configurations, the mold sensor may include a mechanism for exciting the growth surface. For example, a piezoelectric substrate may be incorporated to facilitate excitation of the growth surface. The growth surface and electrical contact system may be configured similar to FIG. 16 through FIG. 18. For example, the growth surface may include a pair of conductive strips with a piezoelectric material between. The piezoelectric substrate may be electrically coupled to the control device 116. Electrical contact may be achieved as previously discussed herein using electrodes or contacts on the rollers. The control device 116 may actuate the piezoelectric substrate (e.g., by applying a voltage or current at a predetermined level or profile) to cause movement or deformation of the growth surface at a given frequency or amplitude defined by the excitation. The control device 116 may stop actuating the piezoelectric substrate and measure the oscillation and/or damping. Measurement may be via an optical sensing device or electrical sensing device. In some configurations, the measurement may be performed using signals from the piezoelectric substrate. For example, the vibrations may cause a voltage across the piezoelectric substrate.

The piezoelectric substrate may be used as a sensor for other configurations such as the audio-based sensing configurations. The piezoelectric substrate may generate an electrical signal when pressure from the sound waves interacts with the piezoelectric substrate. The piezoelectric substrate may act as a microphone and may be used to measure the deflection or movement of the growth surface caused by sound waves. The piezoelectric material may be disposed on the substrate/growth surface between at least two conductive regions. The piezoelectric material may be configured to generate an electrical signal at the conductive regions based on a deflection of the substrate/growth surface. The piezoelectric material may be configured to cause a deflection of the substrate/growth surface responsive to a voltage applied across the conductive regions.

The substrate may be structured as a cantilever, an array of cantilevers, bridges, an array of bridges, a diaphragm or array of diaphragms, and a plate. In some configurations, independent mechanical structures may be configured to promote growth of different molds. Measuring the mechanical properties of each independent structure may allow identification of the types of mold that are growing.

Excitation of the growth surface may also be achieved by an electromagnet interacting with the growth surface. For example, a conductive strip of nickel or ferromagnetic material may be attracted to the electromagnet. The control device 116 may be configured to pulse the electromagnet to cause vibrations of the growth surface. An optical sensor may then be employed to measure the oscillations and/or damping of the growth surface. Mold growth may be determined by comparing the response to the first and second baseline responses taken during the initial phases of the measurement cycle. Electrostatic actuation may also be applied to excite the growth surface. For example, a comb drive or electrostatic motor may be used to excite the growth surface.

The mold sensors may be configured for prolonged use for continuously sensing mold in an environment. Such configurations may utilize the surface exchange mechanism to continually advance the growth surface so that multiple measurement cycles may be performed. In some configurations, the surface exchange mechanism may be an interchangeable cartridge that permits a new growth medium to be installed to continue testing. Some sensor configurations may be well suited for an interchangeable configuration. For example, configurations in which the sensing device is incorporated into the housing may be well-suited for these applications. Configurations that include part of the sensing device below the growth surface may require additional cost for each replacement cartridge.

The surface advancement mechanism may be configured to identify a lack of availability of a new growth surface. For example, the tape-based surface exchange mechanism of FIG. 11 may not be able to advance the growth surface when there is no more unused tape. This may be detected by an increase in torque or inability to change the speed of the driven spool 1106. The control device 116 may be configured to detect this and notify the user that additional measurements are not possible. In other configurations, the last growth surface that can be moved to the chamber may be given different properties. For example, last growth surface may be given a different characteristic that may be recognized by the sensing device. For example, the last growth surface may be transparent or mirrored to change the intensity of light detected by an optical sensor. The control device 116 may be configured to detect the change during a baseline measurement and flag the condition.

The mold sensor may also be configured as a one-time use device to detect mold a single time. The mold sensor may be configured with an interchangeable cartridge that does not advance the growth surface. The one-time use application may be better suited to some sensor configurations such as variants that measure the mechanical properties. For example, the mold sensor may define a slot that permits a growth surface (e.g., a slide or strip) to be inserted manually. Upon completion of the measurement cycle, the growth surface may be manually removed and discarded. In some configurations, the growth surface may be cleaned and retreated with nutrients and reused.

In some configurations, a continuous measurement configuration may be configured to clean and retreat the growth surface. For example, a tape-based configuration may include an electromechanical wiper/scraper mechanism that scrubs the growth surface after the mold destruction phase. The surface exchange mechanism may be configured with a removable waste bin that collects the waste. The surface exchange mechanism may be configured to reapply nutrients on the growth surface. For example, the growth surface may be moved through a reservoir of nutrients or a nutrient solution may be sprayed or dripped onto the growth surface.

The sensing device configurations described herein may be combined in a given application. The mold sensor may utilize more than one of the sensing technologies described to better measure the mold growth or different properties that are indicative of mold growth.

The growth of mold and the rate of mold growth may be affected by temperature. Different types of mold may have different responses to a given temperature. Referring again to FIG. 1, the thermal control element 120 may be controlled by the control device 116. The thermal control element 120 may be operated to influence the growth of mold within the chamber 103. The control device 116 may implement a closed-loop temperature control within the chamber 103 by controlling the thermal control element 120 with temperature feedback from the chamber environment sensor 118. The control device 116 may be configured to select a temperature setpoint to optimize mold growth within the chamber 103 for a given type of mold. The control device 116 may be configured to adjust the temperature setpoint to detect the presence of different types of mold. An open-loop strategy may also be implemented in which the control device 116 is programmed to activate the thermal control element 120 with a predetermined profile.

The control device 116 may be configured to operate the mold suppressor 108 to influence mold growth. The control device 116 may operate the mold suppressor 108 to determine a strength of the mold. The control device 116 may operate the mold suppressor 108 in short bursts that are configured to kill weaker mold spores. The control device 116 may operate the mold suppressor 108 to modulate the growth rate of the mold. The control device 116 may further operate the mold suppressor 108 to prevent saturation of the chamber 103 by destroying some of the mold. The control device 116 may be configured to perform sensor measurements before and after application of the mold suppressor 108 to identify differences in the mold concentration that may have occurred. The control device 116 may be configured to identify a rate of mold destruction during activation of the mold suppressor 108. The rate of mold destruction may be used to identify the type of mold that is growing.

The mold suppressor 108 may be configured to output different UV wavelengths to measure the effect of the different UV wavelengths on mold destruction. The mold suppressor 108 may be configured such that the intensity of light may be varied. The control device 116 may control or select the intensity of the light and the UV wavelength during the mold destruction phase. The control device 116 may operate different light sources that provide different wavelengths of light or filter elements with one or more broadband light source. When the control device 116 has determined that a particular type of mold is present, the control device 116 may be configured to select a UV wavelength that is effective for destroying the particular type of mold that is present. The control device 116 may store data regarding the preferred parameters for the mold suppressor 108 for destroying different types of mold.

The mold sensors described may be operated automatically. For example, the control device 116 may be configured to schedule a measurement cycle at predetermined time intervals. The control device 116 may be configured to determine trigger conditions for initiating a measurement cycle. For example, the control device 116 may monitor weather information from the external sensors or network to determine if conditions are present for mold growth. For example, the control device 116 may initiate a measurement cycle after detecting an increase in humidity or a decrease in temperature. The control device 116 may also be configured to learn local conditions that result in an increased risk of mold growth. The control device 116 may store measurement results and the associated conditions during the measurement cycle. Over time, the control device 116 may learn that certain conditions are associated with mold growth. When the conditions are detected, the control device 116 may reduce the time between measurement cycles.

Figure 20:
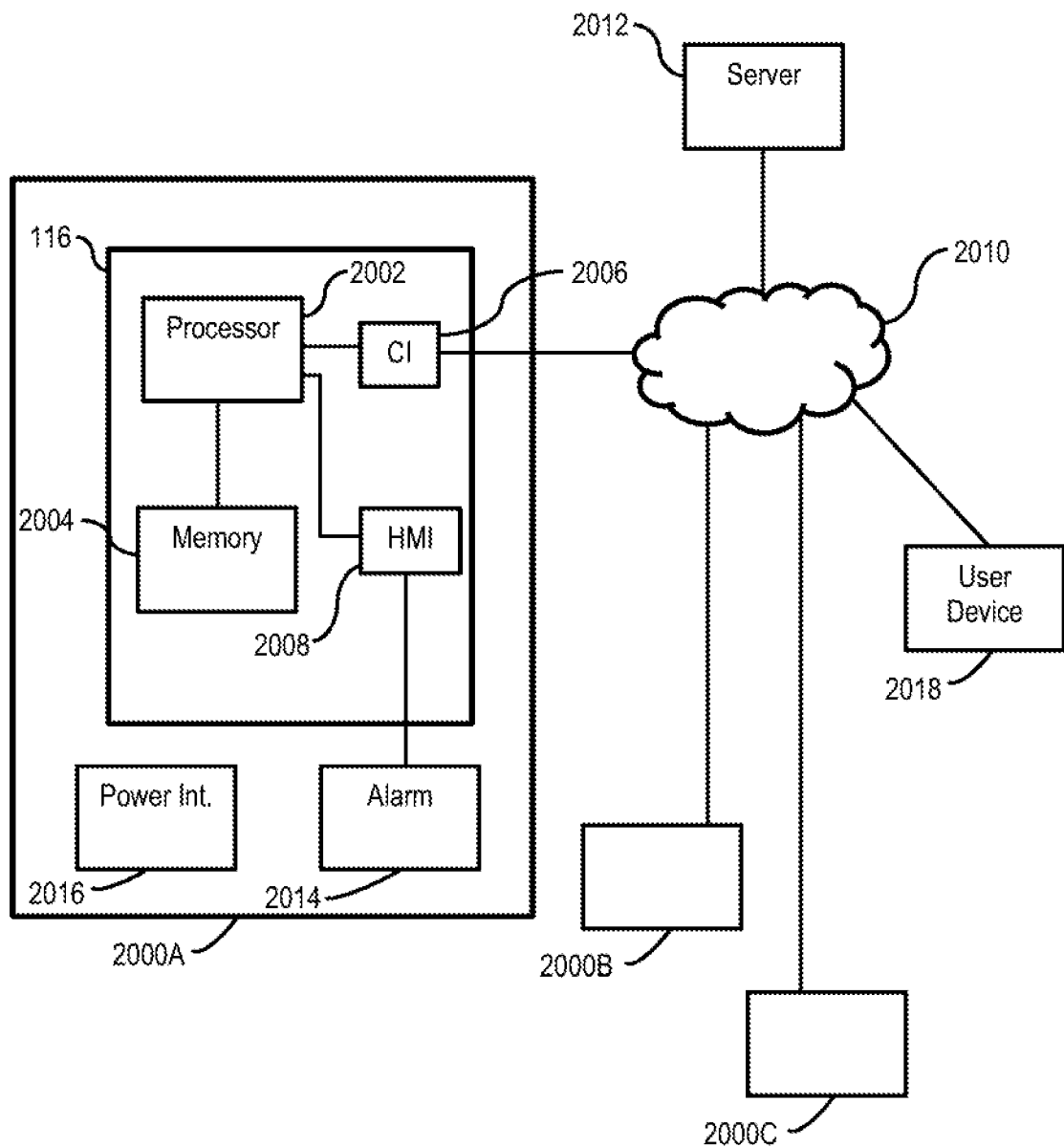
FIG. 20 depicts a mold sensor system including mold sensors and a communication network.

FIG. 20 depicts a possible configuration of the mold sensing system. A mold sensor 2000 may include the control device 116. The control device 116 may include a processing unit 2002 and volatile and non-volatile memory 2004. The mold sensor 2000 may include a Human-Machine Interface (HMI) 2008 for interacting with the user. The HMI 2008 may be a combination of hardware and software elements. The mold sensor 2000 may be operated on demand by the user. The control device 116 may implement the HMI 2008 (e.g., button/light) that permits the user to initiate a measurement cycle. The user may initiate a measurement cycle by pressing a button and a light may indicate that a measurement cycle is in progress. The mold sensor 2000 may further include an alarm 2014 that provides feedback if mold growth threshold is sensed. The alarm 2014 may be a visual alarm such as a light-emitting diode (LED) or display panel. In some configurations, the alarm 2014 may be an audible alarm. The control device 116 may be programmed to activate the alarm 2014 via the HMI 2008 in response to detecting mold concentrations exceeding a threshold during a measurement cycle. The control device 116 may detect greater than normal mold growth when an estimated mold concentration exceeds a predetermined concentration. The alarm may be an audible alarm and/or a virtual alarm that is communicated to the user.

The control device 116 may include a communication interface 2006 that allows a user to communicate with the control device 116 via a cloud or network 2010 (e.g., Ethernet, Bluetooth). The control device 116 may be programmed with a web interface that allows access to the mold sensor parameters via a web browser on a user device 2018 such as a computer or other device. The HMI 2008 may include an application running on the user device 2018 which may be a cell phone or tablet. The HMI 2008 may be configured to permit the user the initiate and/or schedule a measurement cycle. The HMI 2008 may be configured to communicate measurement results to the user. The HMI 2008 may be configured to inform the user about the current status of the mold sensor. For example, the HMI 2008 may communicate the remaining battery life, growth surface or measurement cycles remaining, and warnings related to mold detection. The mold sensor 2000 may include a display module that is driven by the HMI 2008.

The mold sensor 2000 may include a power interface 2016 for providing power to the mold sensor components. The power interface 2016 may include a battery. The battery may be rechargeable. In some configurations, the power interface 2016 may provide a coupling to an external source. For example, power may be provided by a power supply that connects to a household power outlet.

The system may include a plurality of mold sensors 2000 that work cooperatively to determine mold growth and concentrations. In some configurations, the mold sensing system may include a first mold sensor (e.g., 2000A) and a second mold sensor (e.g., 2000B). The first mold sensor 2000A may be located in an area for which excessive mold growth is to be monitored. The second mold sensor 2000B may be located in a reference area. For example, the reference area may be outdoors. The reference area may be an area in which excessive mold growth is not suspected. The second mold sensor 2000B may provide information on mold concentrations that are normally present in the environment. For example, the second mold sensor 2000B may provide mold growth information for a normal amount of mold spores that are naturally present in the environment. The first mold sensor 2000A may provide information on mold concentrations that may be different from the reference area due to being located in an area of active mold growth. For example, the first sensor 2000A may be located in a damp basement in which mold has been growing for some time. The presence of mold in an enclosed area may result in an increased concentration of mold spores in the air when compared to the reference area. By using multiple mold sensors, the system may determine if the concentration of mold is abnormal relative to the reference area.

Using multiple mold sensors may prevent inaccurate assessments. For example, mold spore concentrations may normally vary during the year. By include a reference mold sensor, the normal variations may be subtracted out from the mold assessments of interest. This provides more accurate concentration data for the area of interest and may prevent false warnings due to seasonal variations in mold spore concentrations. For example, the mold sensing system may inhibit a warning when a ratio of the measured mold concentration to the reference mold concentration ratio is less than a threshold. A warning may be indicative that there are more mold spores of certain types on an inside area when compared to an outside area.

In some configurations, the system may evaluate mold growth for different types of mold. For example, a growth surface having differently treated regions and/or a growth surface having regions exposed to different environmental conditions may grow different types of mold. The sensor may be configured to measure the concentration of mold for each region or type of mold. The concentrations of each type of mold may be compared to corresponding reference values from a mold sensor placed in a reference area.

The mold sensors 2000 may communicate with one another via the communication interface 2006. One of the mold sensors 2000 may be configured as a master device. The master device may be configured to manage and coordinate the operation of the other mold sensors. The master device may receive mold growth and concentration data from the other mold sensors. The master device may synchronize measurement cycles of the mold sensors 2000. For example, the master device may send a start measurement cycle signal to the mold sensors to initiate a measurement cycle. The master device may be further configured to determine the mold growth concentration threshold based on data from a reference mold sensor.

The control device 116 may be configured to perform data analysis. The control device 116 may be further configured to collect measurement data and send the data to a server 2012 or cloud computer for processing. The control device 116 may be configured to send measurement data to the user device 2018. An advantage to external processing is that algorithms may be changed in a central location without the need for reprogramming each individual mold sensor. Over time, the algorithms may be improved. In addition, data from many mold sensors can be analyzed to develop improved mold sensing strategies as well as better characterize mold growth.

The user device 2018 may be programmed to coordinate the operation of multiple mold sensors 2000. For example, a program may be executed on the user device 2018 that allows the user to establish communication with the mold sensors 2000. The program may allow the user to identify the mold sensors 2000. For example, the program may allow identification of one of the mold sensors as the reference mold sensor. The program may determine mold alert thresholds based on the data received from the reference mold sensor. The control device 116 may communicate results via the Internet to the user device 2018. This allows placement of the mold sensors 2000 with the capability of remote monitoring. In addition, the program may allow for any number of mold sensors to be added to a mold sensing system.

The mold sensors 2000 may include self-testing capabilities. The control device 116 may be programmed to operate the components to provide confirmation of proper operation. For example, the control device 116 may be configured to detect that the air entry portal 104 is operating properly. Some configurations may include an electric switch or contact that closes when the air entry portal 104 is in a predetermined position. The control device 116 may actuate the air entry portal 104 and monitor the switch or contact to verify proper operation.

The control device 116 may be configured to operate the mold suppressor 108 to confirm proper operation. For example, in configuration with an optical sensing device, the control device 116 may activate the mold suppressor 108 and confirm operation by sampling the optical sensing device.

The control device 116 may be further configured to calibrate the sensing system. The control device 116 may be configured to check the sensor status under conditions in which no mold is growing in order to establish a baseline condition. The control device 116 may check the sensing device prior to exposing the growth surface to the air and/or immediately after exposing the growth surface to air. The resulting signal should be indicative of no mold growth. If the sensing device provides signals that are indicative of mold growth, the mold sensor may require service or need cleaned.

The mold sensor may be used to estimate the mold spore concentration. When the mold sensor is configured with predetermined fixed parameters (e.g., temperature, humidity, pressure, measurement time period), the concentration of mold spores detected in the volume may be correlated with the mold spore concentration from the reference area. For example, mold growth data may be determined to correlate the measured parameter with the concentration of mold. Such a feature may be useful in the design of multi-chamber mold sensors for detecting certain types of mold.

The measurement time may be reduced and detection accuracy improved by implementing mold growth curve fitting and/or pattern recognition algorithms. Mold grows differently in different environments. Curve fitting or pattern recognition may be achieved by changing one of the parameters (e.g., temperature, humidity, pressure) during the measurement. The sensing device may be monitored to determine how the measured properties change in response to the change in the parameter. For example, if the sensor output changes more rapidly at higher humidity than at lower humidity, mold spores may exist. This allows mold detection without having to wait for mold spores to grow to large concentrations.

Figure 21:
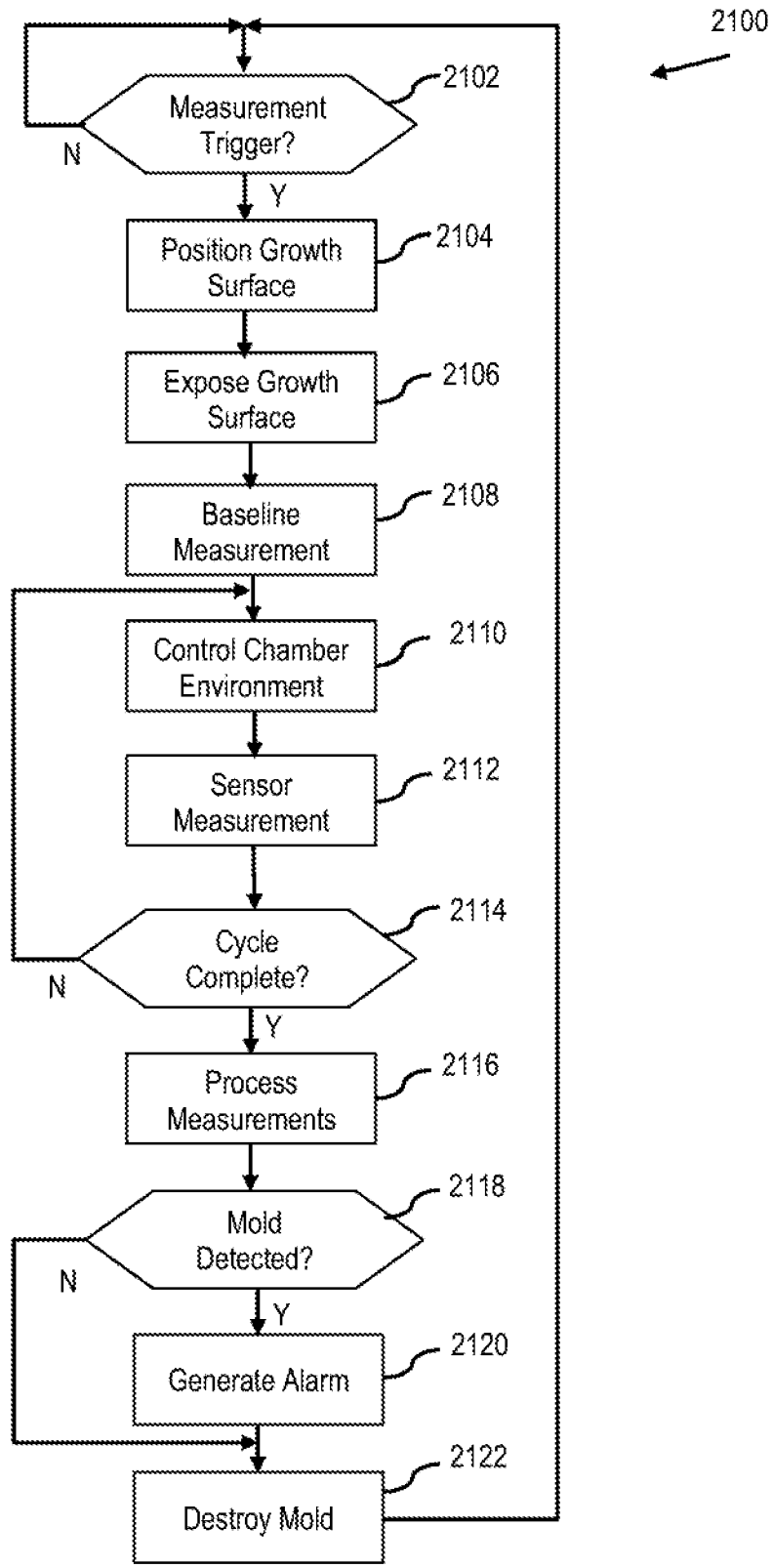
FIG. 21 depicts a flowchart for a possible sequence of operations for operating the mold sensor.

FIG. 21 depicts a flowchart 2100 for a possible sequence of operations for operating the mold sensor configurations. At operation 2102, a check may be performed to determine if a measurement trigger condition is present. For example, the measurement may be manually triggered by a button or switch, commanded via the network, and/or scheduled. In some configurations, the control device 116 may determine a trigger condition based on environmental conditions. The trigger conditions may include a check to determine that there is sufficient growth surface available to perform the measurement (e.g., tape remaining exceeds amount needed for measurement). If there is not trigger condition, operating 2102 may be repeated.

If the measurement trigger condition is satisfied, operation 2104 may be performed to position the growth surface. A measurement cycle may begin by first positioning an unused portion of the growth surface to a position at which it can receive airflow. In configurations with a movable growth surface, the control device 116 may actuate the surface exchange mechanism to advance the growth surface to a predetermined position. For example, an unused portion of the growth surface may be advanced into the growth chamber. In some configurations (e.g., FIGS. 6 and 7), the growth surface may be positioned in an exposed region outside of the growth chamber.

At operation 2106, the growth surface may be exposed to air. For example, the control device 116 may open the air entry portal to permit airflow into the growth chamber. The air entry portal may be opened for a predetermined time period and then closed. The predetermined time period may be determined based on environmental conditions detected from the environment sensors. In some configurations, an airflow sensor or pressure sensor may be monitored to determine when to close the air entry portal.

At operation 2108, a baseline measurement of the particles that attached to the growth surface may be performed. Prior the baseline measurement, the air entry portal may be closed. The baseline measurement may depend on the type of sensing technology being used. For example, in a gas/chemical sensor configuration, mVOCs in the closed chamber may be sensed and recorded. For an optical sensor, the properties of light/electromagnetic waves reflected from or transmitted through the growth surface may be measured.

If there are mold spores attached to the nutrient-rich growth surface, mold will begin to grow. At operation 2110, the chamber environment may be controlled to predetermined parameters. The control device 116 may be configured to enhance the growth environment by operating the thermal control element(s) 120. The control device 116 may operate the thermal control element 120 to increase the speed of mold growth. In addition, any additional system for promoting mold growth may be activated (e.g., humidity control).

At operation 2112, sensor measurements may be performed. The control device 116 may make measurements using the one or more sensing devices during the growth period and compare the results to the baseline measurement. For example, the control device 116 may monitor the change in mVOCs during the growth period. For an optical sensor, the properties of reflected or transmitted light may be monitored.

At operation 2114, a check may be performed to determine if the measurement cycle is completed. For example, a measurement cycle may be complete after a predetermined duration. In some configurations, the sensor data may be monitored and the measurement cycle may be terminated if mold growth is detected. If the measurement cycle is not complete, operation 2112 and operation 2114 may be repeated.

If the measurement cycle is completed, operation 2116 may be performed to process the sensor data. The presence of mold may be determined by comparing the sensor data to stored data that is indicative of mold growth. The amount of mold growth may be back-calculated to determine the concentration of mold spores using algorithms such as Quantitative Polymerase Chain Reaction (QPCR). The processed measurements may include the mold detection data from other mold sensors coupled within the same communication network. A mold concentration from a reference sensor may be compared to the other measured mold concentrations. The control device 116 may be programmed to change a signal indicative of mold growth based on changes detected in the sensor measurements. For example, the control device 116 may make periodic measurements and compare the results to the baseline measurements.

At operation 2118, a check may be performed to determine if mold is detected as described previously herein. For example, if the ratio of the measured mold concentration to a reference mold concentration exceeds a threshold, the system may indicate that mold is present. If mold is detected, operation 2120 may be performed to generate an alarm or warning signal. A signal indicative of mold growth may be generated and output. The alarm or warning may be sent to and displayed on the user device 2018. After generating the warning or indication, operation 2122 may be performed. If no mold is detected, operation 2122 may be performed. The signal indicative of mold growth may be an indicator that mold growth has been detected in a sample. In some configurations, the signal indicative of mold growth may be an indicator that an amount or ratio of mold in the air exceeds a predetermined threshold. In some configurations, the signal indicative of mold growth may be an indication of a measure of the amount of mold present in the sample or the air.

At operation 2122, the control device 116 may operate the mold suppressor to destroy any mold that may have grown. The control device 116 may sample the sensing device during the destruction phase to detect any changes to ensure that the mold is being destroyed. The entire process may then be repeated.

The mold sensor configurations provide that ability to monitor mold growth in an environment over time. The enclosed volume provides a controlled environment for mold growth that allows for more rapid detection of mold. In addition, the enclosed volume allows mold growth without allowing the mold to spread to other areas. Further, after the measurement cycle, the mold suppressor can be activated to destroy the mold that was grown. The surface exchange mechanism permits the growth surface to be exchanged to enable additional measurement cycles. The mold sensor permits continuous monitoring of an area for a period of time.

Some configurations of the growth surface may permit identification of the type of mold that is growing. The sensing device may be configured to measure mold growth in a particular region of the growth surface. In this manner, the mold sensor may determine the type of mold that is growing. The mold detection device is configured to grow mold from mold spores that are present in the air at the time of sampling. The device is configured to deduce or back-calculate to determine the concentration of mold spores in the air that was sampled.

The mold detection device may be used in a variety of manners. In some applications, the mold detection device may be used to determine an absolute measurement of the mold concentration. In other applications, the mold detection device may be used to indicate if the mold concentration exceeds a threshold that is indicative of a mold issue (e.g., threshold mold sensor). In some applications, the mold detection device may be configured to provide a yes/no indication of a presence of mold. The mold growth rate on the growth surface depends on the quantity of mold spores inoculated on the growth surface. The inoculation is correlated to the concentration of mold spores in the air. The mold detection device may be placed in an environment for a predetermined duration of time. The mold detection device may be configured such that the detection of mold growth at the end of the time duration is indicative of the concentration of mold spores in the sampled air being above a threshold. The threshold may be selected to indicate a mold issue in the environment in which the mold detection device is placed. If there is no detection of mold growth at the end of the time duration, the concentration of mold spores in the sample air is less than the threshold and is indicative of the absence of a mold issue.

The threshold mold sensor may be configured to target a predetermined type of mold. For example, the nutrient platform may be configured to permit the growth of the predetermined type of mold. Nutrients may be added to the growth surface that favor growth of the predetermined type of mold.

In other examples, the mold sensor may be configured to target a plurality of mold types. In these configurations, the growth relationships between the plurality of mold types may be investigated and understood. For example, the growth or presence of one type of mold may inhibit the growth of a second type of mold. Understanding the relationship allows the mold sensor to be constructed to minimize such conditions. In addition, the environmental parameters such as temperature and humidity may be controlled to encourage mold growth.

The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in a software executable object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A mold sensor comprising:
   a housing defining a chamber;
   a substrate treated to promote mold growth and exposed within the chamber;
   a plurality of electrical contacts arranged on the substrate, wherein mold growth on the substrate affects electrical properties between the electrical contacts;
   a controller programmed to apply a voltage across pairs of the electrical contacts and measure a current passing through the electrical contacts, and output a signal indicative of mold growth on the substrate based on a change in the electrical properties derived from the voltage and the current; and
   one or more rollers configured to move the substrate into and out of the chamber and wherein the rollers include conductive contacts about a circumference of the rollers that interact with the electrical contacts to establish connection between the controller and the electrical contacts.

2. The mold sensor of claim 1, wherein the voltage is an alternating current (AC) voltage.

3. The mold sensor of claim 2, wherein the controller is further programmed to sweep a frequency and a magnitude of the voltage.

4. The mold sensor of claim 1, wherein the controller is further programmed to estimate a capacitance between the electrical contacts based on the voltage and the current and generate the signal responsive to changes in the capacitance.

5. The mold sensor of claim 1, wherein the controller is further programmed to measure a baseline impedance characteristic before mold growth and generate the signal based on differences between an impedance measurement and the baseline impedance characteristic.

6. A mold sensor comprising:
   a housing defining a chamber;
   a substrate treated to promote mold growth and exposed within the chamber;
   a plurality of electrical contacts arranged on the substrate, wherein mold growth on the substrate affects electrical properties between the electrical contacts;
   one or more electrodes mounted to a frame below the substrate, each of the one or more electrodes including a compliant mechanism to bias each of the one or more electrodes to contact one of the electrical contacts in the plurality of electrical contacts; and
   a controller programmed to apply a voltage across pairs of the electrical contacts, measure a current passing through the electrical contacts, and output a signal indicative of mold growth on the substrate based on a change in the electrical properties derived from the voltage and the current.

7. The mold sensor of claim 6, wherein the voltage is an alternating current (AC) voltage.

8. The mold sensor of claim 7, wherein the controller is further programmed to sweep a frequency and a magnitude of the voltage.

9. The mold sensor of claim 6, wherein the controller is further programmed to estimate a capacitance between the electrical contacts based on the voltage and the current and generate the signal responsive to changes in the capacitance.

10. The mold sensor of claim 6, wherein the controller is further programmed to measure a baseline impedance characteristic before mold growth and generate the signal based on differences between an impedance measurement and the baseline impedance characteristic.

11. A mold sensor comprising:
- a housing defining a chamber;
- a substrate treated to promote mold growth and exposed within the chamber;
- a plurality of electrical contacts arranged on the substrate, wherein mold growth on the substrate affects electrical properties between the electrical contacts;
- one or more magnets mounted to a frame below the substrate and configured to interact with the electrical contacts to attract the substrate; and
- a controller programmed to apply a voltage across pairs of the electrical contacts, measure a current passing through the electrical contacts, and output a signal indicative of mold growth on the substrate based on a change in the electrical properties derived from the voltage and the current.

12. The mold sensor of claim 11, wherein the voltage is an alternating current (AC) voltage.

13. The mold sensor of claim 12, wherein the controller is further programmed to sweep a frequency and a magnitude of the voltage.

14. The mold sensor of claim 11, wherein the controller is further programmed to estimate a capacitance between the electrical contacts based on the voltage and the current and generate the signal responsive to changes in the capacitance.

15. The mold sensor of claim 11, wherein the controller is further programmed to measure a baseline impedance characteristic before mold growth and generate the signal based on differences between an impedance measurement and the baseline impedance characteristic.

16. A growth surface for a mold sensor comprising:
- a substrate treated with nutrients to promote mold growth; and
- first and second generally parallel conductive strips on the substrate, the first conductive strip including first and second gaps to form first, second, and third conductive strip portions, the second conductive strip including third and fourth gaps to form fourth, fifth, and sixth conductive strip portions, the first, second, third, and fourth gaps formed at predetermined intervals corresponding to a size of a chamber in which the substrate is housed, and the first and third conductive strip portions of the first conductive strip and the fourth and sixth conductive strip portions extend away from the chamber.

17. The growth surface of claim 16, wherein the substrate is divided into a plurality of regions and each of the regions is treated with nutrients for growing different types of mold.

* * * * *